(12) United States Patent
Yamashita

(10) Patent No.: US 11,015,171 B2
(45) Date of Patent: *May 25, 2021

(54) IMMORTALIZED STEM CELLS AND METHOD FOR PRODUCING SAME

(71) Applicant: QUARRYMEN & Co. Inc., Tokyo (JP)

(72) Inventor: Yasuhiro Yamashita, Tokyo (JP)

(73) Assignee: QUARRYMEN & Co. Inc., Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 15/967,903

(22) Filed: May 1, 2018

(65) Prior Publication Data

US 2019/0017030 A1  Jan. 17, 2019

Related U.S. Application Data

(63) Continuation of application No. PCT/JP2016/082975, filed on Nov. 7, 2016.

(30) Foreign Application Priority Data

Nov. 5, 2015 (JP) .............................. JP2015-217428

(51) Int. Cl.

| | |
|---|---|
| *C12N 5/00* | (2006.01) |
| *C07K 14/025* | (2006.01) |
| *C07K 14/82* | (2006.01) |
| *C12N 15/867* | (2006.01) |
| *C12N 5/0775* | (2010.01) |
| *C12N 15/09* | (2006.01) |
| *C07K 14/005* | (2006.01) |
| *C12N 9/12* | (2006.01) |
| *C12N 15/86* | (2006.01) |

(52) U.S. Cl.
CPC .......... *C12N 5/0664* (2013.01); *C07K 14/005* (2013.01); *C07K 14/82* (2013.01); *C12N 9/1276* (2013.01); *C12N 15/09* (2013.01); *C12N 15/86* (2013.01); *C12N 2510/04* (2013.01); *C12N 2710/20022* (2013.01); *C12N 2740/15043* (2013.01); *C12N 2740/16043* (2013.01)

(58) Field of Classification Search
None
See application file for complete search history.

(56) References Cited

U.S. PATENT DOCUMENTS

| 2011/0201110 A1* | 8/2011 | Tezuka ................ C12N 5/0696 435/366 |
|---|---|---|
| 2013/0195991 A1 | 8/2013 | Ueda et al. |
| 2015/0018750 A1 | 1/2015 | Ueda et al. |
| 2018/0071504 A1 | 3/2018 | Hochi et al. |

FOREIGN PATENT DOCUMENTS

| CA | 2868251 | * 10/2013 |
|---|---|---|
| JP | 2004-000497 A | 1/2004 |
| JP | 2010-046019 A | 3/2010 |
| JP | 2016-210730 A | 12/2016 |
| WO | 2011/118795 A1 | 9/2011 |
| WO | 2013/118877 A1 | 8/2013 |
| WO | 2016/175164 A1 | 11/2016 |

OTHER PUBLICATIONS

Transfection—Wikipedia. https://en.wikipedia.org/wiki/Transfection. Downloaded on Mar. 17, 2019.*
Harui et al. Frequency and Stability of Chromosomal Integration of Adenovirus Vectors. J. Virol., 1999, 73: 6141-6146.*
Theile et al. ATP-binding cassette transporters as pitfalls in selection of transgenic cells. Analytical Biochemistry 399 (2010) 246-250.*
"Can gentamicin sulfate be used instead of G-418 for neo resistance selection in mammalian cells?" https://www.quora.com/Can-gentamicin-sulfate-be-used-instead-of-G-418-for-neo-resistance-selection-in-mammalian-cells. Downloaded on Mar. 19, 2019.*
"Genticin" https://medical-dictionary.thefreedictionary.com/Genticin. Downloaded on Mar. 19, 2019.*
Koch et al. Transduction of human embryonic stem cells by ecotropic retroviral vectors. Nucleic Acids Res. Oct. 2006; 34(18): e120.*
GenBank: AF015950.1. *Homo sapiens* telomerase reverse transcriptase (hTRT) mRNA, complete cds. Dated Aug. 16, 1997.*
GenBank: AF486310.1. Human papillomavirus type 16 strain E-P isolate PWH-Q42 E6 protein (E6) gene, complete cds. Date Aug. 12, 2002.*
GenBank: AB663783.1. Human papillomavirus type 16 E7 gene for early protein E7, complete cds, isolate: J07-115. Dated Apr. 13, 2013.*
GenBank: AY893260.1, Synthetic construct *Homo sapiens* clone FLH058092.01X B lymphoma Mo-MLV insertion region (BMI1) mRNA, complete cds. Dated Mar. 16, 2005.*

(Continued)

*Primary Examiner* — Nianxiang Zou
(74) *Attorney, Agent, or Firm* — Locke Lord LLP

(57) ABSTRACT

The purpose of the present invention is to provide immortalized stem cells for producing culture supernatant that can be used in the treatment of human diseases. Provided is a method for producing immortalized stem cells, the method being provided with: a step for producing a DNA fragment that includes a telomerase reverse transcriptase and at least one gene selected from the group consisting of Bmi-1, human papilloma virus E6, and human papilloma virus E7; a step for producing a viral vector that incorporates the DNA fragment including the gene; a step for transfecting the viral vector into mammalian stem cells and introducing the gene into the stem cells; and a step for culturing the stem cells into which the gene was introduced and using a drug to select immortalized stem cells.

17 Claims, 8 Drawing Sheets

Specification includes a Sequence Listing.

(56) References Cited

OTHER PUBLICATIONS

Hiroshi Terunuma et al., "Clinical study for the safety of diabetes treatment by using culture supernatant from immortalized somatic stem cells", Regenerative Medicine, vol. 14, special extra issue, Feb. 1, 2015, p. 327, P-02-032 and English translation of [P-02-032] 17:00-18:00.

International Search Report dated Jan. 24, 2017, issued for PCT/JP2016/082975.

* cited by examiner

MCS:

```
        Xho I                          Not I
   EcoR I          (Spe I)  Xba I              BamH I
GTGAATTCCTCGAGACTAGTTCTAGAGCGGCCGCGGATCC
CACTTAAGGAGCTCTGATCAAGATCTCGCCGGCGCCTAGG
```

(): It cannot use for cloning, because it is existed in other location

M1: Supercoil DNA ladder marker
  1: SYN4122-1-7 (200 ng)
  2: SYN4122-2-2 (200 ng)
  3: SYN4122-3-3 (200 ng)
  4: SYN4122-4-4 (200 ng)
M2: λ-Hind III digested DNA marker
1% agarose gel

IMMORTALIZED STEM CELLS AND METHOD FOR PRODUCING SAME

TECHNICAL FIELD

The present invention relates to an immortalized stem cell and a method for producing same. In detail, it relates to the immortalized stem cell comprising a plural genes including telomerase reverse transcriptase, and the method for producing thereof.

BACKGROUND ART

Functions of a living body are sometimes damaged due to diseases, injury and the like. The damages are varied: in several cases such damages is spontaneous cure level, and in several cases they beyond the spontaneous cure level. The severe damage beyond the spontaneous cure level should be restored to original state, if possible.

Methods for recovering functions of a damaged tissue caused by a variety reason are roughly classified into transplant therapy and regeneration therapy. The transplant therapy is defined that organs provided from a donor is transplanted to replace them to restore lost functions of a living body.

In contrast, the regeneration therapy is defined that cells or tissues from several person including a patient itself are cultured to be processed to form the organs; and then they are replaced to those with injuries to repair or regenerate them by using the stem cells. At present, three types of cells such as a human somatic stem cell, a human embryonic stem cell (ES cell), and human induced pluripotent stem cell (iPS cell) are applied or said that they are applicable to the regeneration therapy.

Here, the human somatic stem cell, which has been already used in a study, exists in adult tissues. Therefore, autologous transplantation by using autologous somatic cells does not cause rejection reaction by immune response, and gives good engraftment. Furthermore, there is no report that long term cultivation of these stem cell results in transforming them into tumor cells. However, it is known that the somatic stem cell except "mesenchymal cell" existing in a bone marrow or adipose cells can be only differentiated into specific tissues and organs. And, it is also known that the collection of the somatic stem cell from the human tissue accompanies invasion, and the somatic stem cell is capable passage number are limited to forty and several times, namely, 100 to 200 days being calculated in terms of day numbers.

Human embryonic stem cell (ES cell) is the stem cell which is taken out "inner cell mass" in surplus embryo (blastocyst) obtained from reproductive medicine and the like to be cultured. Since it forms teratoma as an index for its pluripotency, it is considered that it may be differentiated into any one of tridermic phase. There is a report that it could be differentiated into myocardium, nerve, and retina. Since ES cell is an immortalized cell strain, one strain among them is continuously cultured endless. Then, it is known a product having even properties as the cell is manufactured in large scale that under the proper culture conditions.

On the other hand, a fertilized ovum is utilized to product ES cell so that it requires strict handling not so as to cause ethical problems. Also, they are basically hetero-transplantation; it requires means to prevent a rejection response by an immune response. Further, it is known that they requires heterologous cell or serum, when the cells are cultured; and they easily form the teratoma (benign tumor), if the very few number of undifferentiated cells are mixed in a transplanted regenerated tissue.

Human induced pluripotent stem (iPS) cell is established by introducing a part of genes which are specifically expressed in the ES cell into a human adult cell (dermis and the like). If autologous iPS cells are used, the immune rejection problem does not occur; the differentiation technique can be employed for ES cell as is. And, the iPS cell does not use the fertilized ovum which is used in ES cells, but uses an adult tissue to enable to produce a cell having the same quality as that of the embryonic stem cell. There is no problem of the rejection response by the immune response when the autologous iPS cell is utilized.

On the other hand, it is known that the cells are easily turn into benign tumor cells or cancer cells (embryo cell tumor) and the ratio of the cells established as iPS cells is low; because the morphologically similar cells to ES cells are selected from the whole cells to which genes are introduced.

The use of the stem cell itself in the regeneration therapy has the problems described above. Therefore, a method for using biological factors produced by the various stem cells, not but using the stem cells by themselves, for example, a variety of growth factors is searched (WO 2011/118795, herein below, it is referred to as a "prior art 1").

The prior art 1 discloses that a culture sup produced by the cell, which is not immortalized, includes the growth factors such as vein epithelial cell growth factor (VEGF), hepatocyte growth factor (HGF), insulin-like growth factor (IGF), platelet-derived growth factor (PDGF), transformation growth factor-$\beta$ (TGF-$\beta$) and the like, and the growth factors are able to be used as a composition for repairing and regenerating the specific damaged area.

PRIOR ART DOCUMENTS

Patent Documents

Patent Document #1: WO 2011/118795 A1

SUMMARY OF INVENTION

Problems to be Solved by the Invention

However, the prior art 1 discloses lined cells established for normal cells. It is known that telomere of the normal cells shorten in every passage so that the normal cell cannot cell division after 50 to 60 passages and have cell death in general.

Namely, the cell disclosed in the prior art 1 is an aging cell, and they have a problem that it becomes senescent, namely compositions of growth factors in culture supernatant produced therefrom are varied time-dependently. This means that it is impossible to obtain the culture supernatant with stable composition thereof, and it causes the problem that the treatment agent having stable quality is not provided. Therefore, there are strong social needs to establish a lined cell which have infinite growth capability.

On the other hand, as the normal cell being capable of unlimited growth, there is mentioned cancer cell. This is caused by the cancer cell which is out of control to grow unlimitedly, although such growth and division of the normal cell is under control of the living body. Therefore, even if the cell may grow unlimitedly, the cancerous changed one may not be used; because the cells may produce biological factors harmful for the living body.

Namely, in order to use the supernatant as the pharmaceutical preparation, it should have continuously stable amount and compositions of the cell having the infinite growth produced when the immortalized stem cells are used. Therefore, there is a strong need to establish the immortalized cell which is not cancerous, but has the infinite growth ability.

Means for Solving the Problems

The present invention is completed under the above-mentioned situations.

Namely, the first aspect of the present invention is a method for producing an immortalized stem cell comprising the steps of: producing DNA fragment comprising 3 genes selected from the group consisting of Bmi gene, human papilloma virus E6 gene and/or human papilloma virus E7 gene, and telomerase reverse transcriptase gene (TERT); constructing a virus vector to which said DNA fragment comprising said genes; introducing said genes into a mammal dental pulp stem cell by transfecting said virus vector to said cell; and culturing said immortalized dental pulp stem cell to which said gene is introduced to select said immortalized dental pulp stem cell by using a drug.

Here, said DNA fragment preferably comprises any one of gene set selected from the group consisting of (a) bmi-1 gene, human papilloma virus E6 gene and TERT; and (b) human papilloma virus E6 gene, human papilloma virus E7 gene and TERT. Also, said telomerase reverse transcriptase is preferably derived from human.

Said virus is preferably any one of virus selected from the group consisting of lentivirus, adenovirus, and retrovirus, and more preferably it is lentivirus. Said mammary stem cell is preferably any one of the cell selected from the group consisting of a human dental pulp stem cell, a swine dental pulp stem cell, and a swine adipocyte stem cell.

Said drug is preferably an antibiotic, and preferably GENETICIN. The method of the present invention further comprises the step of cloning said selected immortalized stem cell.

The second aspect of the present invention is an immortalized stem cell produced by any one of the method for producing said immortalized stem cell as described above. Here, said cell preferably enables to divides at least 200 PD. Also, a STRO-1 expression amount thereof at 200 PD is preferably almost equal to that of stem cell which is not immortalized.

Advantageous Effect of the Invention

According to the present invention, the genes described above are incorporated into their chromosomes so that these genes are stably expressed. As a result, the cells having divisional ability at least 200 PD is effectively obtained.

Also, according to the present invention, the genes number to be incorporated is at least 2. Therefore, the immortalized stem cell is obtained by using convenient operations compared to the cells to which many genes are introduced.

BRIEF DESCRIPTION OF THE DRAWINGS

FIG. 2A shows positive control, FIG. 2B shows SYN4122-1-7, FIG. 2C shows SYN4122-2-2, FIG. 2D shows SYN4122-3-3, and FIG. 2E shows SYN4122-4-4, respectively.

FIG. 6A is the graph showing the relative indexes of gene expression in transfected cells or the pool cell by using either of virus vector #1 or #2; FIG. 6B is the graph showing these expression in transfected cells or the pool cell by using either of virus vector #3 or #4.

MODE FOR CARRYING OUT THE INVENTION

Figure 1:
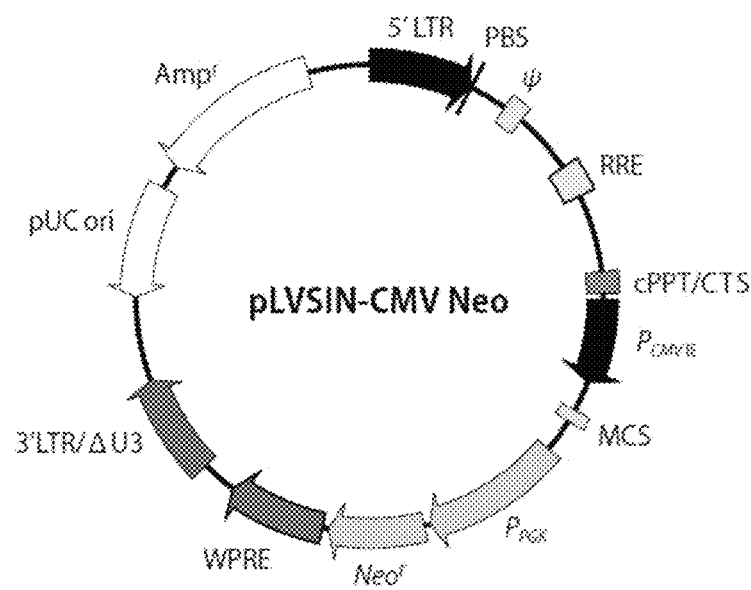
FIG. 1 is a schematic figure showing a structure of a lentivirus plasmid vector pLVSIN-CMV Neo.
Figure 2A:
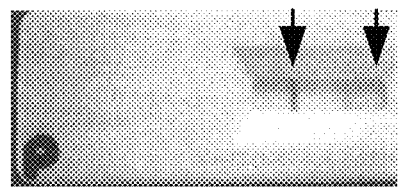
FIGS. 2A-2E show a result for confirming whether the lentivirus plasmid vector exists in the cell or not.
Figure 2B:
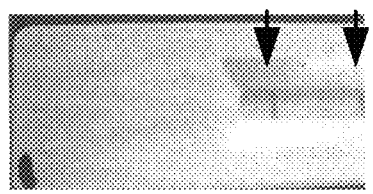
Figure 2C:
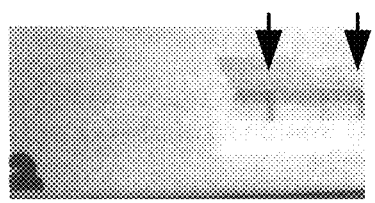
Figure 2D:
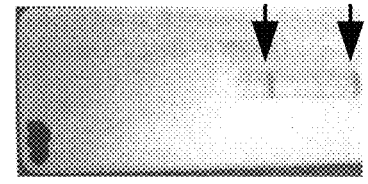
Figure 2E:
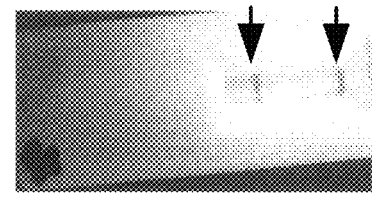

The method for producing the immortalized stem cells of the present invention, it comprises following steps of: (1) producing DNA fragment comprising 3 genes selected from the group consisting of Bmi gene, human papilloma virus E6 gene and/or human papilloma virus E7 gene, and telomerase reverse transcriptase gene (TERT); (2) constructing a virus vector to which said DNA fragment comprising said genes; (3) introducing said genes into a mammal stem cell by transfecting said virus vector to said cell; and (4) culturing said immortalized dental pulp stem cell to which said gene is introduced to select said immortalized dental pulp stem cell by using a drug.

By using the preparation method comprising the procedures (1) to (4), the stem cell, on which all of the genes for immortalization of the cells are stably expressed, is obtained. On the other hand, thus obtained immortalizes stem cells are obtained as cell population which consist of plurality of the cells having genes inserted in different sites, not but the same site on chromosomes (Herein below, such cell population is sometimes referred to as simply the "pool cell"). Therefore, the method is further comprising the step for cloning for choosing such a pool cell.

Herein below, the method of the present invention and the immortalized cells by using the method are explained in detail.

1. Step for Preparing DNA Fragments and Virus Vectors
1.1 Preparation of DNA Fragments to be Incorporated into the Virus Firstly, sequence information of the vector, which is used for incorporating the DNA fragment, is obtained. In the present method, any one of the virus selected from the group consisting of lentivirus, adenovirus, and retrovirus is preferably used as a vector for gene transduction, because it enables to non-transient gene expression of the transduced genes. Lentivirus is preferably used, because it has high production efficiency for the gene transduced cells which stably express thereof.

Hereinbelow, it is explained by using Lenti-plasmid vector (pLVSIN) is raised as an example. For example, the sequence information of pLVSIN is downloaded from TakaraBio web catalogue for confirming multi-cloning sites.

Next, DNA fragments are prepared as follows. In the present invention, 2 to 4 genes are introduced into the DNA fragments for preparing the immortalized stem cells. The cells used are not particularly limited when they are stem cells obtained from mammals. However, the swine dental pulp tissue or human dental pulp tissue are preferably used as the source, because they are easily obtained and stem cells with stable properties are produced.

Also, as the genes to be introduced here, gene set comprising at least 2 genes selected from the group consisting of two early genes of papilloma virus, telomerase reverse transcriptase (TERT), and bmi; because stem cells with stable properties are produced. The early genes of papilloma virus are preferably human papilloma virus E6 or human papilloma virus E7, because of expression efficiency.

It is preferable to prepare and employ the DNA fragments comprising any one of the gene set: (a) bmi gene, human papilloma virus E6 gene and TERT; (b) human papilloma virus E6 gene, human papilloma virus E7 gene and TERT.

Among the genes described above, TERT is the gene of telomere sequence coding an enzyme for extending telomere that is shortened age dependently. Both of human papilloma viruses E6 and E7 are the early genes of human papillomavirus; it is known that E6 reactivates TERT or decompose a protein having PDZ domain. The gene, bmi-1, is known as that it is one of polycomb group member, and relates to self-replication or differentiation control of the stem cells.

By transducing the gene set as mentioned above, it enables to confirm that which combination of the genes gives the efficient expression thereof or immortalization of the cells Hereinbelow, preparation of the lentivirus vector and insertion of 2 genes into them are explained below. In order to insert papilloma virus E7 gene and telomerase reverse transcriptase (hTERT), the set (a), for example, the double strand DNA of EcoRI/KoZal/E7/T2A4/hTERT/BamHI (Sequence No. 1 in the sequence listing) is synthesized by using the standard procedure according to the sequence information. Obtained DNA fragments are cloned into the multi-cloning sites of the lenti plasmid vector (pLVSIN-CMV Neo) by using the standard procedure to obtain a lenti vector (E7T), which has 2 genes described above.

As the same as described above, other 2 genes are inserted. For example, when the set (b) is used, firstly, EcoRI/KoZal/Bmi-1/T2A4/hTERT/BamHI double strands DNA including Bmi-1 (Sequence No. 2 in the sequence listing) is synthesized by using the standard procedure. Obtained DNA fragments are cloned into the multi-cloning sites of the lenti plasmid vector (pLVSIN-CMV Neo) by using the standard procedure to obtain a lenti vector (BT), which has 2 genes described above.

As the same as described above, other 3 genes are inserted. For example, T2A3E6 double strand DNA is synthesized according to the sequence information, and then it is inserted between Bmi-1 and T2A4 included in the lentivirus vector manufactured in the (v2) to prepare EcoRI/KoZal/Bmi-1/T2A3/E6/T2A4/hTERT/BamHI double strand (Sequence No. 3 in the sequence listing). Obtained DNA fragments are cloned into the multi-cloning sites of the lenti plasmid vector (pLVSIN-CMV Neo) by using the standard procedure to obtain a lenti vector (BE6T), which has 2 genes described above.

As the same as described above, other 4 genes are inserted. For example, E6T2A3 double strand DNA is synthesized, and then it is inserted between Kozak sequence of E7T and E7 included in the lentivirus vector (E7T) manufactured in the (d) to prepare EcoRI/KoZal/E6/T2A3/E7/T2A4/hTERT/BamHI double strand (Sequence No. 4 in the sequence listing). Obtained DNA fragments are cloned into the multi-cloning sites of the lenti plasmid vector (pLVSIN-CMV Neo) by using the standard procedure to obtain a lenti vector (E6E7T), which has 3 genes described above. Above-mentioned DNA fragment synthesis may be order to a consignee who accepts such DNA synthesis.

Figure 7:
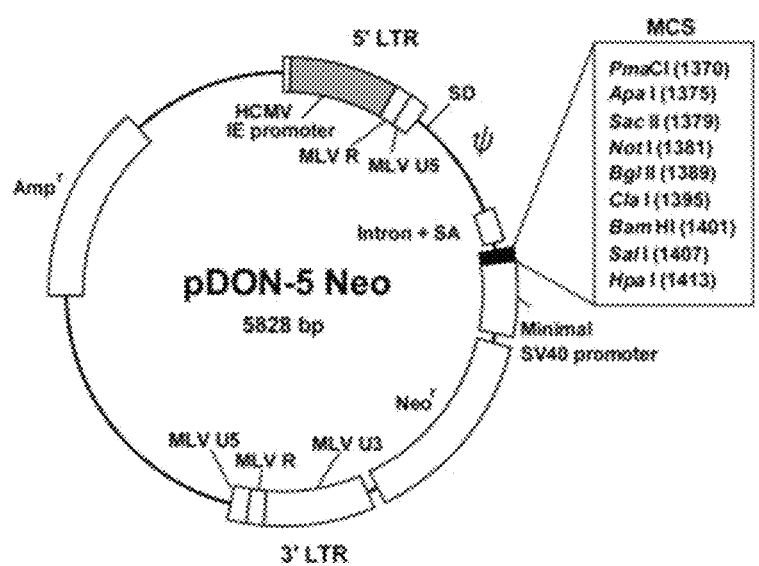
FIG. 7 is the schematic figure showing the structure of retrovirus vector, pDON-5 Neo. In the figure, MCS indicates the multi-cloning sites, and the restriction enzyme r be used for gene introduction is described under PmaCI (1370).

When the retrovirus is used, the procedure is different from that the lentivirus is used. It is conducted that vectors inserted each gene is prepared and then they are co-infected for transduction. For example, 5 immortalized genes to which Kozak sequence (gccacc) is respectively added to the upstream of a start codon (hTERT (Seq. No. 5 in the sequence listing), human papilloma virus E6 (Seq. No. 6 in the sequence listing), and human papilloma virus E7 (Seq. No. 7 in the sequence listing), pigTERT (Seq. No. 8 in the sequence listing), and hBmi-1 (Seq. No. 9 in the sequence listing) are prepared by using the conventional method. Then they are closed into the PmaC I-Hpa I site of pDON-5 N EO DNA (TaKaRa Code 3657: see FIG. 7) to obtain retrovirus plasmid vectors (pDON-5 Neo hTERT vector, pDON-5 Neo HPV16E6 vector, pDON-5 Neo HPV16E7 vector, pDON-5 Neo pHTERT vector and pDON-5 Neo hBmi1 vector).

After that, *E. coli* is transformed by using 5 plasmid DNAs as prepared above according to the conventional method. Then the obtained transformants are cultured in a $CO_2$ incubator to obtain plasmid DNA with transfection grade.

Next, G3T-hi cells are plated in a desirable size plate at 5.5 to $6.5 \times 10^6$ cells/dish, and cultures in the 5% $CO_2$ incubator at about 37° C. for about 20 to 28 hours. Then, desirable transfection agent, for example, 0.3 to 0.5 mL of TransIT-293, is added into the medium to choose 3 plasmid vectors among 5 of them. After that, both of pGP and pE-Ampho (both of them are vectors attached to Retrovirus Packaging Kit Ampho) are co-transfected and then cultures for 40 to 56 hours under the same conditions to insert these genes into the cells.

1.2 Preparation of the Vector Producing Cells

In parallel with the above-mentioned procedures, recombinant lentivirus vector production cells are prepared. As the cell lines, for example, Lenti-X 293T (Clontech Laboratories, Code No.: 632180) and other commercially available lined cells may be used. For the culture of Lenti-X 293T, a medium supplemented with fetal bovine serum and antibiotics may be used. As the medium, for example, minimal essential medium (MEM), Dulbecco's modified Eagle medium (DMEM) and the like are mentioned. For example, DMEM (SIGMA Inc., St. Louis, Mo.) containing 5 to 15% of fetal bovine serum (FBS, Hyclone), 0.5 to 2% of antibiotics (penicillin/Streptomycin, GIBCO) and the like may be preferably used because of cell growth efficiency.

For example, DMEM supplemented with 10% of fetal bovine serum and 1% of penicillin/Streptomycin is prepared for the used as a basal medium. In the specification, it is referred to as "293T basal medium".

For example, when Lenti-X 293T is used as the cell line, cell suspension including 1 to $5\times10^5$ cells/mL is prepared, and 10 mL of the suspension is plated into dish with 10 cm diameter. Then, the dish is incubated in 5% $CO_2$ incubator for about 24 hours, and then passed until use depending on their cell conditions. When they are used, firstly, supernatant of the cultured cells, which are actually passed, are removed and then cells are washed with PBS. After that, a commercially available release agent is added to the cells to release them from the bottom surface of the dish to collect. Next, a desirable volume of the cell suspension, which is diluted 3 to 5 times, is takes out, and trypan blue staining solution is added for cell counting on a hemocytometer. About $5\times10^5$ cells/mL of the cell suspension is prepared by using the basal medium, and for example, the cells are plated in the dish at desirable concentration, and then incubated under the desirable conditions. For example, 1 to $4\times10^6$ cells/mL of the cells are plated into the collagen coat dish with the diameter of 6 cm, and then they are incubated in the 5% $CO_2$ incubator at about 37° C. for about 24 hours. After that, culture medium is changed with fresh one for further incubation.

As the retrovirus preparation cells, G3T-hi cell (Takara Bio Inc.) is preferably used. The cell is prepared from a cell line of 293T (G418-resistant) derived from human kidney cell transformed with hygromycin resistant gene to be inserted human N-acetyl glucosaminyl transferase III (N-acetyl glucosaminyl transferase II: GnT-III).

The G3T-hi cell is designed so as to transiently produce high titer of recombinant viruses by co-transfecting a vector plasmid for gag-pol gene and env gene, and a recombinant retro virus vector plasmid to which target genes are inserted by using Retrovirus Packaging Kit Eco or Ampho (Takara Bio Inc., Code Nos.: 6160, 6161). Because, the G3T-hi cell is 293T origin, it has T-antigen genes of SV40 and they functions to amplify retrovirus RNA, thereby virus solution has high titer is obtained. In general, the virus solution including $10^5$ to $10^7$ cfu/mL is obtained in transient expression by using Retrovirus Packaging Kit.

Sugar chains on the G3T-hi cell membrane are modified with GnT-III. Since budded retrovirus wears host cell membrane, it is assumed that the sugar chain on the membrane protein of the recombinant retrovirus obtained from the G3T-hi cell is modified with GnT-III. By glycosylation, the retrovirus prepared by using the G3T-hi cell has high affinity to RetroNectin (a recombinant fibronectin fragmernt). Therefore, the use of RetroNectin as a coating agent of culture vessel highly improves the gene transduction efficiency to the target cells. RetroNectin is particularly effective for the gene transduction for hematopoietic cell as the target.

When G3T-hi cell is used, the medium which is composed of DMEM containing glucose (4.5 g/L) and L-glutamine (584 mg/L) supplemented with 10% FBS and 1% penicillin/Streptomycin is preferably used instead of the 293T basal medium, because of the retrovirus production efficiency.

1.3 Preparation of the Virus Vector

Hereinbelow, it is explained by using the lentivirus vector as an example.

As described above, the lentivirus vector plasmid prepared as described above is added to the dishes containing culture cells respectively for co-transfection. For such a co-transfection, commercially available packaging system, for example, Lenti-X HTX packaging system (Clontech Laboratories Inc.) and the like may be used. According to manuals attached to them, concrete procedures may be conducted.

After co-transfection, the medium are replaced with fresh complete medium, and incubated at about 37° C. for 24 to 28 hours. Titration of the virus vector is conducted for deciding the timing for recovery, and the culture supernatant including virus vector is recovered when the virus titer becomes maximal. For the titration of the virus vector, the commercially available convenient titration kit, for example, there are mentioned such as Lenti-X GoStix (Clontech Laboratories Inc.) and the like.

For example, next day of the medium change, the culture supernatant in a petri dish is taken out by using desired size of a syringe to collect them. The collected supernatant is filtrated to obtain the virus vector. For example, the supernatant is taken out by using 10 mL of disposable syringe (Terumo Corporation), and then, for example, 0.45 μm of a filter (MILEX-HV, Millipore limited) is attached to the syringe, the virus vector solution is collected into, for example, 15 mL of tube, filtrating the culture supernatant in the syringe.

Next, a reagent included in the commercially available convenient titration lit is used for confirming whether the recombinant lentivirus vector is present or not. For example, the desirable volume of the virus vector solution, for example, 20 μL, is added to S of the Lenti-X GoStix, and Chase Buffer 1 is further added to the solution, and reacted at the desirable temperature and time, for example 10 minutes. Presence of the recombinant lentivirus vector is confirmed with/without appearance of bands.

Cells harboring 4 plasmids (E7T, BT, BE6T and E6E7T) obtained as described above are streaked on an agar medium. Formed colonies are picked up for plating in the desirable medium, for example, 2 mL of LB medium containing antibiotics, and then they are vigorously cultured in a shaker at about 37° C. for 8 hours.

Next, for example, the described volume, 100 μL, of cultivated solution of the cells cultured as describe above is inoculated into 50 mL of LB medium containing a different antibiotic, for example, ampicillin. Then they are vigorously cultured in a shaker at about 37° C. for about 14 to 18 hours.

Volume of the plasmid eluted with water is determined by using the commercially available kit, for example, MN NucleoBond Xtra Mid Kit (Clontech Laboratories Inc.). Together with this procedure, analysis for confirming that the inserted DNA are mutually different is conducted by using the desirable gel, for example, about 1% agarose gel. As the analysis marker for the gel electrophoresis, for example, supercoil DNA ladder, λ-Hind II digested DNA and the like maybe used. As described above, the virus vector may be prepared.

2. Preparation for Mammal Stem Cells 2.1 Preparation for the Swine Dental Pulp Stem Cell Swine jaw (which has teeth on lower jaw) from the swine of 5 to 6 month old and mesentery are obtained. According to the following procedure, swine dental pulp stem cells (herein below, they are sometimes referred to as "SHED") are obtained from the swine teeth and the lower jaw.

Firstly, the swine teeth and the lower jaw are disinfected by using appropriate disinfection agent such as Isodine. Then, a crown of the tooth is cut in horizontal direction by using, for example, a diamond point for a dentist and the like. Then, the dental pulp is collected both from the dental crown and dental root portions treated as mentioned above by using, for example, a hand scaler for the dentist and the like.

Obtained dental pulps are chopped by using such as an ophthalmic knife to be suspended in a predetermined concentration of collagenase solution, for example, 1 to 3 mg/mL to stand for 1 hour into single cell. Then, they are preliminary cultured in DMEM containing 10% FBS, and 1% of Anti-Anti (Invitrogen, Carlsbad, Calif.) for at 37° C. in 5% $CO_2$ incubator for obtaining the cells for passage.

Until the cell numbers are increased to sub-confluent, the medium is exchanged 2 to 3 times per week. Then, the cells in subconfluent state are released from the dish by using the releasing agent such as Hepes solution containing 0.05% trypsin. After that, the cells are collected under the desirable conditions such as at room temperature, and centrifuged at 1,500 rpm for 3 minutes to be collected. The obtained cells are transferred into the fresh medium and conducted cell passage by using the desirable amount, for example, entire volume.

2.2 Preparation of the Swine Adipose Stem Cell

Adipose tissues are excised from the swine mesenteric by using, for example, a dissecting scissors and knife. The excess tissues are removed and then blood is washed out from them by using saline. Obtained adipose cells are transferred into the desirable medium, for example, DMEM supplemented 5 to 15% of bovine serum and desirable concentration of antibiotics. Then, they are preliminary cultured under the same conditions as described above. Subsequently, they are cultured in the DMEM described above at 37° C., 5% $CO_2$ until they become subconfluent. All of the added amounts are shown as the final concentrations. As such medium, for example, DMEM supplemented with about 10% bovine serum, about 100 U/mL of penicillin and about 100 μg/mL of streptomycin may be used.

Similarly to the swine SHED, the cells were released from the dish by using the releasing agent, and then subjected to centrifugation. Then, the obtained cells are passaged to obtain the adipose stem cells.

2.3 Preparation for Dental Pulp Stem Cells from Human Exfoliated Dens Deciduous Teeth Exfoliated or extracted dens deciduous teeth are obtained from healthy children. These dens deciduous teeth are disinfected by using appropriate disinfection agent, for example, Isodine solution, and then the dental pulp tissues are collected as the same as those for obtaining the swine dental pulp tissues. Obtained dental pulp tissues are digested with in the solution including the desired concentrations of collagenase and dispase, for example, about 3 mg/mL of type I collagenase and about 4 mg/mL of dispase at desired temperature for the desired time, for example, about 37° C. for about 1 hour. Next, the solution is filtrated by using, for example, 70 mm of a cell strainer (Falcon) to separate cells.

The cells thus filtrated are re-suspended, for example, in 4 mL of the above-mentioned medium, and plated into the culture dish for adherent cell culture with desirable diameter, for example, 6 cm. Desirable medium, for example, DMEM supplemented with about 10% FCS, is added to the dish and cultured for desirable period, for example, 2 weeks in the incubator under the conditions of 5% $CO_2$, at 37° C. Adherent cells formed colonies, the dental pulp stem cells, are treated with the desirable releasing agent, for example, about 0.2 mM EDTA containing about 0.05% of trypsin for desirable time period, for example, 5 minutes, at about 37° C. to collect the cells released from the dishes.

Next, the adherent cells collected as described above is plated in such as the dish for the adherent cells (collagen-coat dish), and they are primarily cultured in the incubator under the conditions of, for example, 5% $CO_2$, 37° C. to obtain primary cultured cells. When the cells became sub-confluent or confluent by macroscopic observation, the cells are treated as the same as those described above by using the releasing agent to collect the cells in the dish.

After that, the primarily cultured cells are passaged by using the above-mentioned medium at the desirable concentration, for example, about $1\times10^4$ cells/cm$^2$. The cells passaged 1 to 3 times are employed in experiments. As described above, human exfoliated dens deciduous dental pulp stem cells (SHED) are obtained.

Depending on the necessity, dental pulp stem cells from the swine dens deciduous dental pulp stem cells as described above, swine adipose stem cells and th dental pulp stem cell from the human exfoliated dens deciduous dental pulp stem cells may be poured into vials respectively, and may be cryopreserved −80° C.

3. Preparation of Gene Introduced Cells 3.1 Transgenesis by the Lentivirus Vector The swine dental pulp stem cells, the swine adipose stem cells and human dental pulp stem cells obtained as described above are respectively cultured as mentioned above. The cells reached about 70 to 90% confluent, mycoplasma check are conducted by using a commercially available kit. As the kit, there are mentioned, for example, MycoAlert Mycoplasma Detection Kit (Lonza, LT07-318) and the like.

Next, the lentivirus vector prepared as described above is infected to the cells respectively by using Polybrene reagent, and then the cells stably expressing the target genes are selected under selection pressure of the reagent.

The culture supernatant of the cells is respectively removed, and then the cells are respectively washed by using, for example, PBS (pH 7.4). After that, the cells are released from the dish by using the desirable releasing agent, and then respectively collected. As the releasing agent, for example, StemPro (Registered trademark: GIBCO) may be used for the swine dens deciduous dental pulp stem cells and the swine adipose stem cells; and trypsin—EDTA and then like may be used for human dental pulp stem cells.

Obtained cells are counted according to the conventional method, and then they are plated into each well of, for example, 6-well plate (CORNING) with tissue culture treatment (T. C. treatment) so as to be about $1\times10^5$ cells/well. They are incubated in the $CO_2$ incubator at about 37° C. for about 24 hours to confirm even distribution of the cells in the well.

After that, the culture supernatant is removed. The desired volume of the desired medium containing desired concentration of Polybrene, for example, the desirable amount of DMEM containing about 8 μg/mL of Polybrene and about 10% of FBS, is added for the dental pulp stem cell of the swine dens deciduous dental pulp stem cells or the swine adipocyte stem cells at 750 μL/well. Next, the lentivirus vector solution described above is added into each cell, for example, at about 250 μL/well.

In the case of the human dental pulp stem cell of the dens deciduous teeth, DMEM containing the same amount of Polybrene and FBS is added into the wells at desirable amount, for example, about 1.2 mL/well, and then, the lentivirus vector solution is added to each cell at the desirable amount, for example, about 400 μL/well.

Each plate to which the virus vectors are added as described above is centrifuged under the desirable conditions such as at about 1,000×g for about 30 minutes, at about 32° C. for virus infection of the cells. After that, they are cultured under the desirable conditions such as at about 37° C. in $CO_2$ incubator for about 4 to about 6 hours; and desirable volume of the fresh culture medium, for example, about 1 mL/well, is added into each well. Then, they are cultured under the desirable conditions, for example, at 37° C. in the $CO_2$ incubator for about 24 hours to conduct the gene transduction.

3.2 Selection Under the Presence of the Agents

The culture supernatant of the cultured stem cells (the swine dental pulp stem cells, swine adipose stem cells, and human dental pulp stem cells), which are cultured as described above, are removed from each well of the culture plate. Then, the desirable concentration of the agents for selection, for example, selection medium containing either of about 0.4 mg/mL or about 0.8 mg/mL of GENETICIN (G418, GIBCO) is added into each well in the desirable volume, for example, about 2 mL/well to exchange the culture medium. After that, the cells are cultured for desirable period, for example, about 3 to 5 days exchanging the culture medium for selecting the gene transduced cells.

A portion of the cultured cells are subjected to the cloning, and remains are subsequently cultured in the selection medium as pool cells. The cloning may be conducted as follows.

For example, the selection medium without the antibiotics such as that does not contain penicillin/Streptomycin and G418 is used for cell dilution. The cells are diluted to the desirable concentration, for example, about $1 \times 10^3$ cells/4 mL or about $5 \times 10^3$ cells/4 mL is plated into each dish, and then, they are incubated at about 37° C. in the $CO_2$ incubator for about 24 hours. Formed colonies are marked from the rear side of the dish, and they become the desirable number, for example, about 100; the culture supernatant in the well is removed for washing the cultured cells with PBS. Cloning rings are set in the dishes and the cells from the colonies which are released by using the releasing agent is respectively placed in each well of 48 well plate at the desirable amount, such as about 1 mL.

3.3 Preparation of Total RNA

In order to confirm the gene expression, total RNA is prepared by using, for example, NucleoSpin RNA II (a kit provided by MACHEREY-NAGEL). It is preferable to use the buffers employed in below, the ring filter and the like which are included in the kit, and to perform the procedure according to the manual included in the kit; because those bring total RNA with high purity.

Lysate of cell pellet is prepared from the desirable number, for example, about $5 \times 10^5$ cells, and it is poured into the ring filter with purple color. Then, it is centrifuged under the desirable conditions such as at about 11,000×g for about 1 minute. After the centrifugation, the filter was discarded and then, the desirable amount of ethanol, for example, about 350 μL of about 70% ethanol is added into the collection tube. The solution is mixed with pipetting in desirable numbers such as about 5 times.

Next, the desirable amount of the obtained solution is taken out, for example, about 700 μL and then it is loaded on the ring column with pale blue color set in the collection tube. Then, the tube is centrifuged under the desirable conditions such as about 11,000×g for about 30 seconds to bind RNA. After the centrifugation, the column is set in the new collection tube. Then, the desirable reagent such as about 350 μL of MDB is added into the tube, and centrifuged under the desirable conditions such as at about 11,000×g for about 1 minute for desalination.

After the centrifugation, DNA reaction mixture is prepared by mixing lightly, for example, the desirable amount of rDNase, for example, about 10 μL with that of DNase reaction buffer, for example, about 90 μL. The desirable amount of the mixture, for example, about 95 μL is added to the column, and incubated under the desirable conditions such as at room temperature for about 15 minutes to digest DNA. Subsequently, the desirable amount, for example, 200 μL of buffer RA2 is the column and they are centrifuged under the desirable conditions such as about 11,000×g at about 30 seconds to wash. Subsequently, the column is set in the new collection tube, and the desirable amount such as about 700 μL of buffer RA3 is added to the column for the further centrifugation under the desirable conditions such as about 11,000×g for about 30 seconds.

Subsequently, eluted solution in the collection tube is discarded, and the desirable amount, for example, about 250 μL of the buffer RA3 is again added to the column for the centrifugation under the desirable condition, for example, at about 11,000×g for about 2 minutes to sir-dry a silica membrane of the column. The column is set in the desirable size such as about 1.5 mL of the collection tube, and the desirable amount of RNAase-free water, for example, about 60 μL is added to the column. Then, the column is centrifuged under the desirable conditions such as about 11,000×g for about 1 minute to obtain total RNA sample.

3.4 Reverse Transcription

The total RNA sample obtained as describe above is subjected to reverse transcription. Subsequently, it is subjected to real time PCR to obtain PCR products. In order to conduct the reverse transcription, for example, commercially available kit such as PrimeScript RT reagent Kit (Perfect Real time, TaKaRa Bio) according to the manual attached thereof.

The real time PCR is conducted by using the commercially available kit, for example, SYBR Premix Ex Taq and the like. Also, as the genes employed here, there are mentioned, for example, such as swine β-actin, human β-actin and the like. As primers, for example, those listed in the sequence Nos. 10 to 15 are prepared for use.

Firstly, the desirable amount, for example, Premix for real time PCR is prepared by mixing about 350 μL of SYBR Premix Ex Taq II (×2), about 28 μL of Primer mix (about 10 μL) and about 266 μL of redistilled water. Next, the desirable amount of Premix, for example, about 23 L is poured into each tube for real time PCR, and about 2 μL of the template cDNA into each tube. Then, real time PCR is conducted under the desirable conditions, for example, at about 95° C. for about 30 seconds, about 40 cycles of (at about 95° C. for about 5 seconds, and then at about 60° C. for about 30 seconds). Subsequently, amplified products are released under the desirable conditions, for example, at about 95° C. for about 15 seconds, at about 60° C. for about 30 seconds, at about 95° C. for about 15 seconds to obtain a melting curve. For the human dental pulp stem cells, the same procedures are conducted.

From the calibration curve described above, the expression levels of the transduced gene by using each virus vectors may be obtained. By using the calibration of internal standards, accurate results may be obtained.

In each gene-transduced stem cell, it is confirmed that the transduced genes are expressed. By this, insertion efficiency of the genes by using each plasmid may be obtained.

Next, the gene-transduced cells (hereinbelow, they are sometimes referred to as the "transduced-gene stably expression cell population" or the "pool cells".) is subjected to single cell cloning.

Firstly, the pool cells are plated in the desirable size dish with desirable concentration, for example, in the dish having 60 mm diameter with about $1 \times 10^3$ cells/dish and they are cultured in $CO_2$ incubator at the desirable temperature and time, for example, at 37° C. for 24 hours. After that, the growth medium containing the selection reagents described above are exchanged, and further cultured to form colonies. Each formed colonies are respectively taken out by using both of the cloning ring and the releasing agent and to desirable plate, for example, 24-well plate.

The plated cells are grown and then, they are plated into the culture dish and the like to grown for expanding culture (cell expansion). By this, the transduced-gene stably expression cell is obtained as a single clone. Next, the obtained clone is cultured as described above for grown then to obtain total mRNA. The obtained total RNA is used as the template for reverse transcription by using the desirable kit, for example, PrimeScript RT reagent Kit to obtain template cDNA.

After that, real time PCR is conducted similarly to those described above by using, for example, cDNA (reverse transcription products) as the template, the above-mentioned SYBR Premix Ex TaqII (Tli RNaseH Plus), the primers (specific primers for the gene-transduced cells or the internal standard genes respectively, for example, the primers shown as Seq. Nos. 10 to 15).

Ct value obtained by using the secondary differentiation curve from the real time PCR is plotted on X-axis, and the relative total RNA value is plotted on Y-axis to prepare the calibration curve for expression determination amount of each gene. When the expression amount of the pool cell equals 1, relative index of these of the transduced-genes derived from the swine dental pulp stem cell or these derived from human dental pulp stem cell is obtained. By this, it is confirmed whether all of the transduced-genes are expressed, or obtain the expression amount thereof is obtained for selecting the clone as the target.

As described above, both of the immortalized stem cell population and cloned immortalized stem cell therefrom may be obtained.

EXAMPLE (Example 1) the Preparation of Virus Vector (No. 1)

(1) The Preparation of Cells for Virus Preparation
(1-1) The Reagents and the Like, and Wake-Up of the Cells As the recombinant lentivirus vector production cell line, Lenti-X 293T (Clontech Laboratories Inc., code No.: 632180) is used. For culturing Lenti-X 293T, DMEM (SIGMA, code No.: D5796-500ML) containing 10% fetal bovine serum (FBS, Hyclone, Lot No.: GRD0051) and antibiotics (1% penicillin/Streptomycin, GIBCO, code No. 15140-122) was used. In the present specification, hereinbelow, the medium is referred to as "293T basal medium". Freeze dried cells (Cellbanker, code No.: BLC-1) was purchased from Nippon Zenyaku Kogyo Co., Ltd.

Firstly, Lenti-X 293T cells were suspended in 293T basal medium, and a portion thereof was taken out and diluted 8 times. 140 µL of trypan blue staining solution was added into 20 µL of the diluted medium for cell counting by using the hemocytometer. Cell concentration was $2.94 \times 10^6$ cells/mL. 10 mL of the obtained suspension was transferred into the centrifuge tube together with 4 stored vials including $2.0 \times 10^6$ cells. The centrifuged tubes were centrifuged at 200×g for 3 minutes, at room temperature to collect the cells. The supernatant of the collected cells were removed completely, and the cells were suspended in necessary amount of the cell stage solution to prepare the cell suspension. The suspension was dispensed at 1 mL/vial, and then they were stored at −80° C. Depending on the necessity, they were transferred into liquid nitrogen in a container on next day for the stage.

(1-2) Preparation of the Recombinant Lentivirus Vector Production Cells

DMEM, the antibiotics, and FBS were the same as those used in (1-1). Also, phosphate buffered saline (PBS (−), code No.: 10010-049, hereinbelow, it is sometimes simply referred to as "PBS".) were purchased from GIBCO. The T. C.-treated dishes having 10 cm diameter were purchased from Iwaki & Co. Ltd. The releasing agent, 0.25% trypsin—EDTA (1×) was purchased from GIBCO.

10 mL of 293T basal medium was added into 15 mL tube. The suspension in the vials stores in (1-1) was rapidly thawed in a water bath at 37° C., and then they were added into the centrifuge tube. They were centrifuged at 200×g for 3 minutes, at room temperature to collect the cells. As the same as those in (1-1), trypan blue staining was conducted to count the cell numbers by using hemocytometer. The cell number per vial was $2.0 \times 10^6$ cells.

The cells were plated in the concentration from 1 to $5 \times 10^6$ cells/10 mL/10 cm dish, and they were cultured for about 24 hours in the 5% $CO_2$ incubator. After that, they were passes until use according to the cell conditions.

(2) The Preparation of the Recombinant Lentivirus Vector
(2-1) Reagents and the Like DMEM, the antibiotics, FBS, the releasing agent, and PBS were the same as those used in (1-1). Collagen coated dishes having the diameter of 6 cm are purchased from Iwaki & Co. Ltd., and the transfection reagents (TransIT-293, code No.: MIR2700) was purchased from Mirus Bio LCC., respectively. Both of the recombinant lentivirus vector production reagent (Lenti-X™ HTX Packaging System, code No.: 631247, Clontech Laboratories Inc.) and Lenti-X HTX Packaging Mix (VSV-G) were purchased from Clontech Laboratories Inc.

(2-2) Preparation of the Recombinant Lentivirus Vector (Transfection Plasmid)

The following 4 lentivirus vectors were constructed. Those were constructed on the basis of pLVSIN vector sequence information downloaded from the Takara Web Catalogue, according to the following procedures.

(v1) the Lenti Vector E7T (EcoRI/KoZal/E72A4/hTERT/BamHI)

According to the sequence information, the double strand DNS of EcoRI/KoZal/E7/T2A4/hTERT/BamHI (Seq. 1) was synthesized. Then, they were cloned into multi cloning sites of (pLVSIN-CMV Neo, see FIG. 1) by using standard procedure to obtain SYN4122-1-7 (Seq. No. 1 in the sequence listing).

(v2) the Lenti Vector BT (EcoRI/KoZal/Bmi-1/T2A4/hTERT/BamHI)

According to the sequence information, the double strand DNA of Bmi-1 was synthesized and replaced with E7 of the lentivirus vector E7T (Seq. No. 2 in the sequence listing), which was prepared in (v1).

(v3) the Lenti Vector BE6T (EcoRI/KoZal/Bmi-1/T2A3/E6/T2A4/hTERT/BamHI)

According to the sequence information, the double strand DNA of T2A3E6 was synthesized and inserted between Bmi-1 of the lentivirus vector, which was prepared in (v2), and T2A4 (Seq. No. 3 in the sequence listing).

(v4) the Lenti Vector E6E7T (EcoRI/KoZal/E6/T2A3/E7/T2A4/hTERT/BamHI)

According to the sequence information, the double strand DNA of E6T2A3 was synthesized and inserted between Kozak sequence of the lentivirus vector E7T, which was prepared in (v1) and E7 (Seq. No. 4 in the sequence listing).

(2-3) Preparation of the Cells for Co-Transfection

The supernatant of Lenti-X 293T cells passed as described in the (1) (1-2) was removed. Then cells were washed by using PBS and collected by adding the releasing agent into the dish.

From 4 times diluted cell suspension, 50 µL of the portion was taken out, and the equal amount of trypan blue was added thereto. Then, cell numbers counted by using the hemocytometer was $2.38 \times 10^6$ cells/mL. The basal medium as mentioned above was added into the suspension to adjust the cell numbers to $5 \times 10^5$ cells/mL; and then plated into the collagen coat-dishes having 6 cm of the diameter at the concentration of $2 \times 10^6$ cells/4 mL/dish. After that, they were incubated in the 5% $CO_2$ incubator at 37° C. for about 24 hours. The culture medium was exchanged for further incubation.

(2-4) The Transfection of the Lentivirus Vector and Packaging

Co-transfection was conducted by using Lenti-X HTX packaging system (hereinbelow, it is sometimes simply referred to as the "packaging system".). Xfect Polymer was sufficiently vortexed, and 2 micro tubes for each transfection sample (the tube 1 and 2) were prepared. In the tube 1, 179 to 182 µL of Xfect Reaction buffer was added, and 15 µL of Lenti-X 293 T Packaging Mix was further added, and then finally, 3 to 6 µL of the vector plasmid shown in Table 1 (plasmid solution, 200 µL in total). Also, in the tube 2, 197 µL of Xfect Reaction buffer was added, and 3 µL of Xfect Polymer was further added (polymer solution, 200 µL).

TABLE 1

| Vector No. | Name | Seq, length (bp) | Modification at 5' terminal/3' terminal | Conc. (ng/mL) |
|---|---|---|---|---|
| SYN4122-1-7 | LVE7T | 3,780 | EcoRI/BamHI | 543 |
| SYN4122-2-2 | LVBT | 975 | — | 650 |
| SYN4122-3-3 | LVBE6T | 537 | — | 736 |
| SYN4122-4-4 | LVE6E7T | 537 | — | 569 |

These 2 tubes were respectively fully mixed by using vortex; and then the polymer solution was added into the plasmid solution and vortexed with moderate strength to obtain DNA-Xfect mixture. The DNA-Xfect mixture was stood in ambient for 10 minutes to form nanoparticles. Lenti-X 293T cells prepared in (2-3) as mentioned above were taken out from the $CO_2$ incubator, and 2 mL of the medium was removed. Then, entire amount of the DNA-Xfect mixture (400 µL) was dropped therein. The dish was gently swung to penetrate the DNA-Xfect mixture inside of the whole dish.

Subsequently, the dish was again placed in the $CO_2$ incubator and incubated at 37° C. After 4 hours, 2 mL of the Lenti-X 293 T cell strain growth medium, which is composed of DMEM containing the high concentration of the glucose (4.5 g/L), 4 mM L-glutamine, and 3.7 g/L of sodium bicarbonate supplemented with 10% of Tet System Aproved FBS, 1 mM sodium pyruvate (hereinbelow, it is sometimes simply referred to as the "complete medium".) was added, and incubated at 37° C. for overnight.

Next, the medium was exchanged with the fresh complete medium (4 mL), and incubated at 37° C. for 24 to 48 hours. Recovery timing was determined, conducting convenient titer measurement of the virus vector by using Lenti-X GoStix (for 3 tests, Clontech Laboratories Inc.). The culture supernatant containing the lenti virus was collected at the time point when the virus titer became maximal.

(2-5) The Collection of the Lentivirus Vector

In the next day of the medium exchange, the culture supernatant in the dish was aspirated by using 10 mL of the disposable syringe (Terumo Corporation) for the collection. The virus vector solution was collected in the 15 mL of the tube by filtration of the culture medium in the syringe through 0.45 m pore size (MILEX-HV, Millipore) attached thereto. The filtrated culture supernatant collected in the tube was mixed, and then dispensed at 1 ml/vial for storing at −80° C. About 200 µL portion was separately stored as the virus vector solution for titration.

(2-6) Convenient Titration of the Lentivirus Vector

20 µL of the virus vector solution for titration was added to Lenti-X GoStix, and then 4 drops of Chase Buffer 1 were added. Next, they were reacted at ambient for 10 minutes, and then band formation was confirmed. As shown in FIGS. 2 (A) to (E), all of measured SYN4122-1-7, SYN4122-2-2, SYN4122-3-3 and SYN4122-4-4 showed 2 bands, which confirms the existence of the recombinant lentivirus vectors. In the figure, left band shows the reference, and right one shows the recombinant lentivirus vector.

(3) SYN4122 Transfection Plasmid

Lenti-X 293 T cells including 4 plasmids obtained described above (SYN4122-1-7, SYN4122-2-2, SYN4122-3-3 and SYN4122-4-4) were streaked on the agar medium to form colonies. Formed colonies were picked up and plated in 2 mL of LB medium containing antibiotics and cultured with vigorous shaking (200 rpm) at 37° C. for about 8 hours.

Next, 100 µL of the culture broth of the cells cultured described above was transferred into 50 mL of LB medium containing ampicillin, and cultured with vigorous shaking (200 rpm) at 37° C. for about 16 hours.

Figure 3:
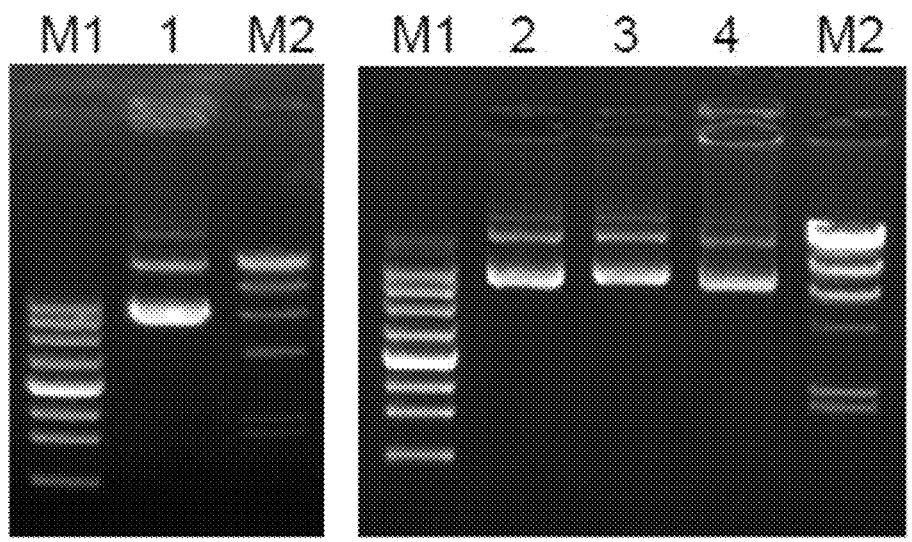
FIG. 3 is an agarose gel electrophoresis of the transfection plasmid.

By using MN NucleoBond Xtra Mid Kit (Clontech Laboratories Inc.), the plasmid was eluted with water and its amount was measured. Along with this, it was analyzed on agarose gel (1%). As the markers, M1 was the supercoil DNA ladder, and M2 was λ-Hind m digested DNA. Results were shown in Table 1 and FIG. 3. Agarose gel electrophoresis result showed that the incorporated DNAs were respectively different.

(Example 2) Preparation of the Virus Vector (No. 2)

(1) Preparation of the Cells for the Retrovirus Preparation
(1-1) Reagents, Wake-Up of the Cells, Etc.

As the retrovirus preparation cell line, G3T-hi cells were used. In order to culture G3T-hi cells, DMEM (SIGMA, code No.: D5796-500 mL) containing glucose (4.5 g/L). L-glutamine (584 mg/L), 10% fetal bovine serum (FBS, Hyclone, lot No.: GRD0051) and the antibiotics (1% of penicillin/Streptomycin, GIBCO, code No. 15140-122) was used.

The cell culture was conducted as the same as those in the case that Lenti-X 293T cells were suspended in the 293T basal medium. From the collected cells, culture supernatant was completely removed and then the cells were suspended in the necessary amount of the cell storage medium to prepare the cell suspension. It was dispensed at 1 mL/vial and stored at −80° C. Depending on the necessity, they were transferred into the container including liquid nitrogen to be stored on the next day.

(1-2) Preparation of the Retrovirus Vector Producing Cells

DMEM, the antibiotics, FBS, glucose and L-glutamine were the same those used in (1-1). PBS, T. C. treated dish having 10 cm diameter of the diameter, and 0.25% trypsin—EDTA (1×) were the same as those used in Example 1.

10 mL of the medium was added into 15 mL size centrifuge tube. The cell suspension in the stored vials in (1-1) were rapidly thawed by warming in the water bath at 37° C. was added into the centrifuge tube. It was centrifuged at 200×g for 3 minutes at ambient to collect the cells. The cells were stained by using trypan blue as the same as those in (1-1) and cell numbers were counted by using the hemocytometer. The cell number per vial was $3.0 \times 10^6$ cells.

The cells were plated at the concentration from 1 to $5 \times 10^6$ ells/10 mL/10 cm dish, and incubated in the 5% $CO_2$ incubator for about 24 hours. After that, they were passed until use, according to the cell condition.

(2) Preparation of the Recombinant Retrovirus Vector (2-1) Reagents and the Like DMEM, the antibiotics, FBS, the releasing agent, and PBS were the same as those used in (1-1). Collagen coated dishes (6 cm), and the transfection reagents (TransIT-293, code No.: MIR2700) were employed those as the same as Example 1. All of Retrovirus Packaging Kit Ampho, Retrovirus Titer Set (for Real Time PCR), and One Step SYBR PrimeScript RT-PCR Kit (all of them were from Takara Bio Inc.) were used.

(2-2) Preparation of the Retrovirus Vector (Transfection Plasmid)

The following 5 retrovirus vectors were constructed. Those were constructed on the basis of pDON-5 NEO vector sequence information, according to the following procedures.

Five immortalized genes to which Kozak sequence (gc-cacc) was added to the upstream of the initial codon (hTERT (Seq. No. 5 in the sequence listing), E6 of human papilloma virus (Seq. No. 6 in the sequence listing) and E7 (Seq. No. 7 in the sequence listing), pig TERT (Seq. No. 8 in the sequence listing), and hBmi-1 (Seq. No. 9 in the sequence listing)) were prepared according to the conventional method, and then they were cloned into PmaC I-Hpa I site of pDON-5 NEO DNA (TaKaRa Code 3657: see, FIG. 7) to obtain 5 retrovirus vectors (pDON-5 Neo hTERT vector, pDON-5 Neo HPV16E6 vector, pDON-5 Neo HPV16E7 vector, pDON-5 Neo pHTERT vector, and pDON-5 Neo hBmi1 vector).

*E. coli* was transformed with 5 plasmid DNAs prepared as described above, according to the conventional method, and the transformants were incubated at 37° C. in the $CO_2$ incubator to prepare respectively the plasmid DNA (about 50 µg) of transfection grade. Each plasmid DNA was dissolved in the sterile water to prepare DNA solution.

(2-3) The Production of the Recombinant Retrovirus Vector

G3T-hi cells were plated in 5 tissue culture dish (100 mm) at the concentration of $6 \times 10^6$ cells/dish, and cultured in the 5% $CO_2$ incubator at 37° C. for about 24 hours. Then, 0.4 mL of the transfection reagent (TransIT-293) was added, and 3 plasmid vectors were chosen from 5 of them for co-introduction of pGP and pE-Ampho (both of them were included in Retrovirus Packaging Kit Ampho). After that, they were further incubated for 40 to 56 hours under the same conditions for introduction of the genes. Then, the cells were further cultured for 48 hours under the same conditions. After the termination of the culture, the culture supernatant including the retrovirus vector was collected and then it is subjected to sterile filtration by using 0.45 µm (Millipore), and then 1 mL of them were dispensed into the tubes.

(2-4) Calculation of the Titer of the Recombinant Retrovirus Vector

The titer of the recombinant retrovirus vector was determined by using Retrovirus Titer Set (for Real Time PCR) or One Step SYBR PrimeScript RT-PCR Kit (Perfect Real Time) (both of them were from Takara Bio Inc.), according to their manuals. Copy numbers of the RNA control template attached in each kit were plotted on X-axis, and the Ct values obtained from the secondary differentiation curve ($2^{nd}$ Derivative) were plotted on Y-axis to prepare the calibration curve. By using the calibration curve, the titers of the test samples were obtained.

DNase I treatment was conducted at 37° C. for 30 minutes, next at 70° C. for 10 minutes, and then cooled to 4° C. by using 12.5 µL of the recombinant retrovirus vector, 2.5 µL of 10×DNase I buffer, 2.0 µL of DNase I (5 U/µL), 0.5 µL of RNase inhibitor (40 U/µL) and 7.5 µL of RNase free sterile distilled water (total amount 25.0 µL). After completion of DNase I treatment, they were rapidly subjected to the real time PCR.

4 primers shown in the following Table 2 were designed and prepared for PCR. The composition of the primer mix for PCR (each 10 µL) was follows: 40 µL of the forward primer (50 µM; the target gene: CH000987-F, the reference gene: HA067803-F)), 40 µL of the reverse primer (50 µM; the target gene: CH000987-R, the reference gene: HA067803-R)), and 120 µL of the sterile distilled water. By using the primer mix for PCR, the real time PCR was performed under the same conditions as those in Example 1.

TABLE 2

| Type of Primers | Symbols | Sequences | Seq. Nos. |
| --- | --- | --- | --- |
| Target Genes | CH000987-F | GCACTGCCCTCAGACTTCAAGA | 16 |
|  | CH000987-R | GCGGGACTATGGTTGCTGAC | 17 |
| Reference gene (human β-actin) | HA067803-F | TGGCACCCAGCACAATGAA | 18 |
|  | HA067803-R | CTAAGTCATAGTCCGCCTAGAAGCA | 19 |

Subsequently, the real time PCR was conducted under the conditions at 42° C. for 5 minutes, at 95° C. for 10 seconds, and then 40 cycles of (at 95° C. for 5 seconds, and then at 60° C. for 30 seconds) by using 12.5 µL of 2× One Step SYBR RT-PCR buffer HI, 0.5 µL of TaKaRa ExTaq HS (5 U/µL), 0.5 µL of PrimeScript RT Enzyme Mix II, 0.5 µL of forward titer primer FRT-1 (10 pmol/µL), 0.5 µL of reverse titer primer FRT-1 (10 pmol/µL), 8.5 µL of RNase free sterile distilled water, and 2 µL of the template (total amount was 25.0 µL). Subsequently, the PCR products were denatured under the conditions such as at 95° C. for 15 seconds, at 60° C. for 30 seconds, and at 95° C. for 15 seconds to obtain renaturation curve. The titer of the test samples (the vectors) are shown in the following Table 3.

TABLE 3

| Vector Nos. | Name of Seq. | Average Titer (copies/mL) |
| --- | --- | --- |
| SYN5587-1-4 | pDON-5 Neo hTERT | $1.46 \times 10^{10}$ |
| SYN5587-2-10 | pDON-5 Neo HPV16E6 | $1.15 \times 10^{10}$ |
| SYN5587-3-7 | pDON-5 Neo HPV16E7 | $4.05 \times 10^{10}$ |

TABLE 3-continued

| Vector Nos. | Name of Seq. | Average Titer (copies/mL) |
| --- | --- | --- |
| SYN5587-4-9 | pDON-5 Neo pTERT | $1.27 \times 10^{10}$ |
| SYN5587-5-1 | pDON-5 Neo hBmi1 | $2.83 \times 10^{10}$ |

(Example 3) Preparation of the Stem Cells

The lentivirus vectors obtained in Example 1 were infected to the swine dental pulp stem cells, the swine adipose stem cells, or human dental pulp stem cells prepared as described below respectively to prepare the strain stably expressing the target genes.

(1) Preparation of the Stem Cells (1-1) The Swine Dental Pulp Stem Cell

From Shokuniku Kosha Co. Ltd. (Minato-ku, Nagoya city, Japan), the jaw (the lower jaw with tooth) and mesentery of 5 to 6 month of swine were obtained. Those immediate after slaughtering were transported in the ice box including the thermal gel (−30° C.). From the swine tooth and the lower jaw, the swine dental pulp stem cells (SHED) were obtained according to the following procedure and transferred to the laboratory.

The transferred swine tooth and the lower jaw were sterilized with Isodine. Then, the crowns of the tooth in the lower jaw were cut in horizontal direction by using the diamond point for the dentist, and cut in the vertical direction along with the pulp space to delete the overcanopy. The dental pulps were collected from the crowns and roots of the tooth treated as described above by the scaler for the dentist.

The obtained dental pulps were chopped by using the ophthalmic knife to be suspended in 2 mg/L of collagenase solution. The solution was placed in the incubator at 37° C. for 1 hr, and the cells were separated. In order to obtain the cells for passage, the separated cells were preliminarily cultured in DMEM (SIGMA, St. Louis, Mo.) supplemented 10% FBS and 1% Anti-Anti (Invitrogen, Carlsbad, Calif.) under the conditions at 37° C. and 5% $CO_2$.

Firstly, in the initial stage of the culture, the cells were cultured until sub-confluent, replacing the medium 2 to 3 times per week. The sub-confluent cells were detached from the flask by using Hepes solution including 0.05% trypsin, and then, the cells were collected by the centrifugation in 1,500 rpm for 3 minutes at room temperature. The obtained cells were transferred into the fresh medium and the entire of the cells were used to the passage culture under the same conditions as described above.

(1-2) The Swine Adipose Stem Cell

From the swine mesenteric, adipose tissues were excised by using a dissecting scissors or knife, and collected. Excess tissues were removed for them and then remains were washed with saline to wash out blood. Obtained adipose cells are transferred into DMEM containing 10% bovine serum, 100 U/mL of penicillin and 100 μg/mL of streptomycin for the preliminary culture under the same conditions as described above. Next, they were cultures in the DME as mentioned above until they became subconfluent under the conditions of 37° C., 5% $CO_2$. All of the added amounts were shown in final concentrations. Similarly to the swine SHED, the cells were detached by using 0.05% trypsin solution to be centrifuged for 3 minutes in 1,500 rpm to be subjected to the passage culture.

(1-3) Dental Pulp Stem Cells from Human Dense Deciduous Teeth

Exfoliated dense deciduous teeth from a healthy 10 years old boy were used. After the teeth were disinfected by using appropriate disinfection agent such as Isodine, the crown of the tooth was cut in horizontal direction by using the diamond point for a dentist. Then, the dental pulp tissue was collected both from the dental crown and dental root portions by using dental reamer. The obtained dental pulp tissue was digested in the solution containing 3 mg/mL of type I collagenase and 4 mg/mL of dispase at 37° C. for 1 hour. Then, they were filtrated by using the cell strainer with 70 mm (Falcon).

The filtrated cells were resuspended in 4 mL of the medium, and plated in the culture dish for the adherent cell having the diameter of 6 cm. DMEM containing 10% FCS was added into the dish, and then incubated for about 2 weeks in the incubator under the presence of 5% $CO_2$ at 37° C. The adherent cells formed the colonies (the dental pulp stem cells) were treated with 0.2 mM EDTA containing 0.05% trypsin for 5 minutes at 37° C., and then release cells from the dish were collected.

Next, the collected cells described above were plated in the culture dish for the adherent cells (the collagen coated dish), and then conducted primary culture in the incubator under the presence of 5% $CO_2$, at 37° C. to obtain the primary cultured cells. When the cells became subconfluent (about 70% of the surface was covered by the cells) or confluent by macroscopic observation, they were treated with 0.2 mM EDTA containing 0.05% of trypsin for 5 minutes, at 37° C. for releasing the cells from the culture dish and then to be collected.

Thus obtained cells were again plated in the dich containing above medium, and passed several times to be grown until the cell number became about $1 \times 10^7$ cells/mL. Obtained cells were stored in the liquid nitrogen.

After that, the primary culture cells were cultured by using the above-mentioned medium at the concentration of about $1 \times 10^4$ cells/cm$^2$. The cells passed 1 to 3 times were used for the experiments. As described above, the human exfoliated dens deciduous dental pulp stem cells (SHED) were obtained. The swine dens deciduous dental pulp stem cells, the swine adipose stem cells, or human dens deciduous dental pulp stem cells were cryopreserved at −80° C.

(Example 4) Preparation of the Cells for Gene Transduction (1) Set Up of the Cells (1-1) Culture of the Swine Dental Pulp Stem Cell and Swine Adipose Stem Cells The culture medium (DMEM containing 10% FBS (GIBCO)) was used for the swine dental pulp stem cells or the swine adipose stem cells. 10 mL of the culture medium was added into the 15 mL size tube. The stored vials containing the swine dental pulp stem cells were rapidly thawed in the water bath at 37° C., and they were added into the tube. They were centrifuged at 200×g for 3 minutes in ambient. After removing the culture supernatant, 10 mL of the culture medium was added to have the suspension. A portion of the suspension was taken out and subjected to trypan blue staining, and then cell numbers were counted by using the hemocytometer. As a result, it was $5 \times 10^5$ cells/vial.

Next, the suspension was plated at the concentration of 1 to $5 \times 10^5$ cells/10 mL/dish in the dish having the diameter of 10 cm (Iwaki & Co. Ltd., T. C. treated) and then incubated in the 5% $CO_2$ incubator at 37° C. for about 24 hours. Then, the cells were observed by using the microscope. The medium in the dish was completely removed, and then 10 mL of the fresh culture medium was added. After that, they were incubated in 5% $CO_2$ incubator at 37° C. for about 24 hours. After that, the cells were continuously passed until use depending on their conditions. The cells were released from the dish by using 0.25% trypsin—EDTA (GIBCO). Further to the swine adipose stem cells, the same procedures were conducted.

(1-2) Human Dental Pulp Stem Cells

For the human dental pulp stem cells, DMEM containing 10% FBS (SIGMA INC.,) was used. Other than that, the same procedures were the same as those in (1-1). Note that the result of the cell counting was $1.0 \times 10^5$ cells/vial.

(Example 5) Selection of the Gene-Transduced Cells and Gene Expression Analysis (the Preparation of the Pool Cells)

(1) Construct of the Lentivirus Vector Gene Transduced Cells

Viable cell numbers among the set up cells described above were counted by using both of the trypan blue staining and the hemocytometer. They were plated in the dishes having the diameter of 10 cm at the concentration of $1 \times 10^6$ cells/10 mL and then they were incubated in the $CO_2$ incubator at 37° C. for about 24 hours. When the cell density reached 70 to 90 percent, confluent, the cells were diluted to the concentration of $1 \times 10^4$ cells/mL and then used to passage. Also, the mycoplasma infection was checked as described in below.

(2) Mycoplasma Check of the Culture Cells

Mycoplasma infection of the cells was checked by using MycoAlert Mycoplasma Detection Kit (Lonza, LT07-318).

Mycoplasma Alert reagent was added into each well of the 96-well plate (Corning, flat bottom) at 100 μL/well. Into the wells, the culture supernatant of the swine dental pulp stem cell or that of the swine adipose stem cell was added at 100 μL/well (6-well each). Pipetting was conducted 5 times for each well. The plate was placed in ambient for 5 minutes; bubbles were removed by using dryer. The measurement A was conducted by using Kinetic Cycles 5 with illuminometer (Tecan (infinite 200, microplate reader with multi-detection mode)).

Next, MycoAlert substrate was added at 100 μL/well, and pipetting was conducted 5 times for each well. The plate was placed in ambient for 5 minutes; bubbles were removed by using dryer. The measurement B was conducted by using Kinetic Cycles 5 with illuminometer. Viable mycoplasma in the sample was lyzed to treat the MycoAlert substrate with enzyme of mycoplasma (Luciferin) to convert ADP to ATP. ATP levels before and after MycoAlert addition were measured, and then results were obtained by using the following equation. When R becomes not less than 1, the result was evaluated as positive; and when R becomes less than 1, it was evaluated as negative. Excitation wavelength was 565 nm. Results are shown in the following Table 4.

R=Average of the measured value B/Average of the measured value A

TABLE 4

| Sample | Measured value A | Measured value B | B/A | Decision |
|---|---|---|---|---|
| Medium (DMEM) | 269 | 136 | 0.50 | Negative |
| Supernatant of Swine Dental Pulp Stem Cell | 266 | 115 | 0.43 | Negative |
| Supernatant of Swine Adipose Cell | 257 | 131 | 0.51 | Negative |
| Positive Control | 1201 | 3712 | 3.09 | Positive |
| Negative Control (without reagents) | 1253 | 183 | 0.15 | Negative |

Further to the human dental pulp stem cells, the same tests were conducted. Results are shown in Table 5. It was confirmed that either cell were not infected by mycoplasma.

TABLE 5

| Sample | Measured value A | Measured value B | B/A | Decision |
|---|---|---|---|---|
| Medium (DMEM) | 250 | 106 | 0.42 | Negative |
| Supernatant of Human Dental Pulp Stem Cell | 264 | 115 | 0.43 | Negative |
| Supernatant of Human Dental Pulp Stem Cell | 276 | 115 | 0.42 | Negative |
| Positive Control | 1256 | 3971 | 3.16 | Positive |
| Negative Control (without reagents) | 1298 | 173 | 0.13 | Negative |

(2) Introduction of the Lentivirus Vector Genes

The lentivirus vector constructed in Example 1 was infected to each stem cell obtained in Example 3 by using polybrene reagent, and then the cells were cultured in the medium supplemented with GENETICIN to select the cell line, which stably expresses the target genes.

After the culture supernatant of respective stem cells as described above was removed, the stem cells were washed with PBS (pH 7.4). Then, the stem cells were release from the dishes by using the releasing agent (StemPro (Registered trademark: GIBCO) for the swine dens deciduous dental pulp stem cells or the swine adipose stem cells; trypsin-EDTA for the human dens deciduous dental pulp stem cells) to be respectively collected. Similarly to those described above, the cell number was counted by using trypan blue staining and the hemocytometer. Then, they were plated in the tissue culture-treatment (T. C. treatment-) 6-well plate (CORNING) of which wells respectively contain suitable volume of the culture medium so as to be $1 \times 10^5$ cells/well, and incubated at 37° C. in the $CO_2$ incubator for about 24 hours. It was confirmed that the cells were evenly grown in entire of the dish.

After that, the supernatant was removed, for the swine dens deciduous dental pulp stem cells or the swine adipose stem cells, DMEM containing 8 μg/mL of polybrene and 10% FBS were added into each well at 750 μL/well, and then, the lentivirus vector solution obtained in Example 1 was added into each well at 250 μL/well.

For the human dental pulp stem cells, DMEM containing 8 μg/mL of polybrene and 10% of FBS was added into each well at 1.2 mL/well, and then the lentivirus vector solution was added into each well at 400 μL/well. As described above, the plate to which the virus vector was added were centrifuged at 1,000×g for 30 minutes at 32° C. for viral infection to the cells. They were incubated at 37° C. in the $CO_2$ incubator for about 4 to 6 hours, and then the culture medium was added into each well at 1 mL/well. Next, they were incubated at 37° C. in the $CO_2$ incubator for about 24 hours for gene transduction.

(3) Selection by Using Drugs

The culture supernatant in the 6 well plate incubated as describe above was removed, and then the medium was exchanged to the selection medium containing 0.4 mg/mL or 0.8 mg/mL of GENETICIN (G418, GIBCO) (2 mL/well). After that, they were cultured for 3 to 5 days for selecting the gene-transduced cells, exchanging the medium. The selection by using the drugs was conducted as the same as those for all of the swine dental pulp stem cell, the swine adipose stem cells and human dental pulp stem cells.

Portions of the respective cultured cells were used for cloning, and remains were continuously cultured in the selection medium as the pool cells. In order for cloning, the cells were diluted by using the selection medium without all of penicillin/Streptomycin and G418, and plated in the dish having the diameter of 60 mm at the concentration of $1 \times 10^3$ cells/4 mL/dish or $5 \times 10^3$ cells/4 mL/dish. Next, they were incubated at 37° C. in the $CO_2$ incubator for 24 hours.

The formed colonies were marked from the rear side of the dish. When marked colony numbers reached about 100, the culture supernatant was removed and colonies were washed with PBS. The cloning ring was set in the dish, and cells from the colonies released from the dish were respectively put in each well of 48-well plate containing 1 mL of the medium. They were continuously cultured at 37° C. in the $CO_2$ incubator for scale-up, observing the cell density therein. After about 2 to 3 weeks from the start of the selection by using the drugs, the grown cell population which became drug resistant, were respectively cryopreserved. They were stored at the concentration of $2 \times 10^6$ cells/vial, when their concentration reached about $5 \times 10^6$ cells/mL.

As the cryopreservation solution, Cellbanker (Zenyaku Kogyo Co. Ltd.) was used for both of the swine des deciduous dental pulp stem cells and the swine adipose stem cells; and for the human dens deciduous dental pulp stem cells, Bambancer (Nippon Genetics)) was used. By using the cryopreservation solution, respective stem cells were frozen at the concentration of $0.5 \times 10^6$ cells//s/vial (for the swine dens deciduous dental pulp stem cells or the swine adipose stem cells) or $1 \times 10^6$ cells/vial (for the human dens deciduous dental pulp stem cells), and then stored at −80° C. until use.

(4) Preparation of the Total RNA

For the total RNA (total RNA), NucleoSpin RNA II (kit purchased from MACHEREY-NAGEL) was used. Firstly, in order to extract RNA for the expression confirmation, cell pellet containing $5 \times 10^5$ cells were prepared. Both of 350 μL of RA1 buffer (included in the kit) and 7 μL of IM DTT (dithiothreitol) sterilized with 0.22 μm filter were added onto the pellet and mixed well to lyze the cells to prepare lysate. The lysate was put in the ring filter with violet color (included in the kit) set in the collection tube, and then they were centrifuges at 11,000×g for 1 minute. After that, the filter was discarded, and 350 μL of 70% ethanol was added into the collection tube. They were pipetted for 5 timed to adjust binding conditions of RNA.

Next, 700 μL of the mixture was loaded on the ring column with pale blue color (included in the kit) set in the collection tube, they were centrifuged at 11,000×g for 30 seconds to bind RNA. After the centrifugation, the column was set in fresh collection tube, and 350 μL of MDB (included in the kit) was added therein, and they were centrifuged 11,000×g for 1 minute to desalt.

After the centrifugation, 10 μL of rDNase (540 μL/vial) and 90 μL of DNase reaction buffer (included in the kit) were gently mixed to prepare DNA reaction mixture. Then, 95 μL of the buffer was added to the column and incubated for 15 minutes in ambient to digest DNA. After the incubation, 200 μL of RA2 buffer (included in the kit) was added to the column, and they were centrifuged at 11,000×g for 30 seconds to wash. Subsequently, the column was set into the fresh collection tube, and 700 μL of RA3 buffer (included in the kit) was added into the column, and then they were centrifuged at 11,000×g for 30 seconds to wash.

After the centrifugation, the solution eluted into the collection tube was discarded and 250 μL of RA3 buffer was again added into the column and further centrifuged at 11,000×g for 2 minutes, and then the silica membrane of the column was air-dried. The column was set in the 1.5 mL size collection tube, and 60 μL of RNAase-free water was added to the column, and they were centrifuged at 11,000×g for 1 minute to obtain total RNA sample with high purity (40 to 60 μL).

(5) Reverse Transcription Reaction

Reverse transcription was conducted by using total RNA sample as described above and PrimeScript RT reagent Kit (Perfect Real time, TaKaRa Bio).

(5-1) Reverse Transcription for PrimeScript RT Reagent Kit

The total RNA sample was diluted to the concentration of 20 ng/μL by using EASY Dilution included in the kit as shown in the following Table 6.

TABLE 6

| | Sample | RNA Conc. (ng/μL) | Dilution Ratio to 20 ng/μL | Sample vol.(μL) | EASY Dilution Added vol.(μL) |
|---|---|---|---|---|---|
| 1 | Swine Dental Pulp NGMC | 446.5 | 22.33 | 1 | 21.3 |
| 2 | Swine Dental Pulp Virus #1 | 224.4 | 11.22 | 2 | 20.4 |
| 3 | Swine Dental Pulp Virus #2 | 332.6 | 16.63 | 1 | 15.6 |
| 4 | Swine Dental Pulp Virus #3 | 361.1 | 18.06 | 1 | 17.1 |
| 5 | Swine Dental Pulp Virus #4 | 286.2 | 14.31 | 1 | 13.3 |
| 6 | Swine Adipocyte NGMC | 264.1 | 13.21 | 1 | 12.2 |
| 7 | Swine Adipocyte Virus #1 | 117.2 | 5.86 | 3 | 14.6 |
| 8 | Swine Adipocyte Virus #2 | 131.5 | 6.58 | 3 | 16.7 |
| 9 | Swine Adipocyte Virus #3 | 227.4 | 11.37 | 2 | 20.7 |
| 10 | Swine Adipocyte Virus #4 | 154.9 | 7.75 | 3 | 20.2 |
| 11 | Human dental pulp NGMC | 428.3 | 21.42 | 2 | 40.8 |
| 12 | Human dental pulp Virus #1 | 266.0 | 13.30 | 2 | 24.6 |
| 13 | Human dental pulp Virus #2 | 309.0 | 15.50 | 2 | 29.0 |
| 14 | Human dental pulp Virus #3 | 265.7 | 13.29 | 2 | 24.6 |
| 15 | Human dental pulp Virus #4 | 375.0 | 18.75 | 2 | 35.5 |

180 μL of Premix (the reaction mixture) including 72 μL of 5× PrimeScript Buffer, 18 μL of PrimeScript RT Enzyme Mix, 18 μL of Random 6 mer (100 μM), and 72 μL of double distilled water (D2W) was prepared. Next, Premix was dispended into PCR tube at 10 μL, and 10 μL of the template RNA was added into each tube. Then, reverse transcription was conducted under the conditions of 37° C. for 15 minutes, at 85° C. for 5 seconds, and cooled to 4° C. The obtained products were subjected to the real time PCR.

(5-2) Real Time PCR by Using SYBR Premix Ex Taq

Premix for real time PCR were prepared by mixing 350 μL of SYBR Premix Ex Taq II (×2), 28 μL of Primer mix (10 μM), and 266 μL of double distilled water. The primers were used at final concentration of 0.4 μM. As the reference genes, both of the swine β-actin and human β-actin were used. The primers having the sequences (Seq. Nos. 10 to 15 in the sequence listing) shown in the following Table 7 were used for PCR. Also, the reference samples were prepared as shown in the following Table 8.

TABLE 7

| Nos. | Nucleotide Sequence | Seq. Nos. |
|---|---|---|
| 1 | GGCACTGCCCTCAGACTTCA | 10 |
| 2 | CTGCTAAAGCGCATGCTCCA | 11 |
| 3 | CTGCGGCATCCACGAACTA | 12 |
| 4 | ACAGCACCGTGTTGGCGTA | 13 |
| 5 | TTGGTCAAGCAGCATAATCCAAAG | 14 |
| 6 | GTCAAGGGCATAGCCTACCACAA | 15 |

TABLE 8

| Sample Nos. | RNA Conc. (ng/μL) | Dilution ratio-> 100 ng/μL | Sample Amount (μL) | EASY Dilution added Amount (μL) |
|---|---|---|---|---|
| 7 Swine Adipose Virus #1 | 117.2 | 1.17 | 15 | 2.6 |
| 12 Human Dental Pulp | 266.0 | 2.66 | 10 | 16.6 |

Premix as describes above was dispensed into the tubes for the real time PCR at 23 μL, and 2 μL of the template cDNA were added into each tube. Next, the real time PCT was conducted under the conditions of at 95° C. for 30 seconds, and 40 cycles of (at 95° C. for 5 seconds, and then at 60° C. for 30 seconds). Subsequently, the products were denatured under the conditions of at 95° C. for 15 seconds, at 60° C. for 30 seconds, and at 95° C. for 15 seconds to obtain the melting curve. The human dental pulp stem cells were treated as the same procedures. Results are shown in the following Tables 9 to 11 and FIGS. 4 and 5.

TABLE 9

| | Titer | Relative index of total RNA (Log (2)) | Ct (STD) *1 |
|---|---|---|---|
| Calibration Curve | $1.28 \times 10^1$ | 3.7 | 30.01 |
| | $6.40 \times 10^1$ | 6.0 | 27.75 |
| | $3.20 \times 10^2$ | 8.3 | 25.22 |
| | $1.60 \times 10^3$ | 10.6 | 22.94 |
| | $8.00 \times 10^3$ | 13.0 | 20.64 |
| | $4.00 \times 10^4$ | 15.3 | 18.45 |
| | $2.00 \times 10^5$ | 17.6 | 16.23 |
| Slope | | | −1.007 |
| Segment | | | 33.844 |
| Amplification Efficiency | | | 1.010 |

TABLE 9-continued

| | Titer | Relative index of total RNA (Log (2)) | Ct (STD) *1 |
|---|---|---|---|
| Relative index (R) | | | −1.00 |
| RSQ (Coefficient of determination, $R^2$) | | | 1.00 |

*1 Obtained from the amplification curve of the reference inserted gene sample derived from swine (secondary differentiation curve)

TABLE 10

| Stem Cell | Sample Nos. | Genes in LV*2 | Value of Swine β - Actin | Relative index |
|---|---|---|---|---|
| Swine Dental Pulp | Virus #1 | E7T*3 | 0.7758 | 1.00 |
| | Virus #2 | BT*4 | 0.3017 | 0.39 |
| | Virus #3 | BE6T*5 | 0.1587 | 0.20 |
| | Virus #4 | B6E7T*6 | 0.6144 | 0.79 |
| Swine Adipose | Virus #1 | E7T*3 | 1.0719 | 1.00 |
| | Virus #2 | BT*4 | 0.3004 | 0.28 |
| | Virus #3 | BE6T*5 | 0.1559 | 0.15 |
| | Virus #4 | B6E7T*6 | 0.5922 | 0.55 |

*2 lentivirus
*3 Human papillomavirus E7, human telomerase reverse transcriptase (hTERT)
*4 bmi, hTERT
*5 bmi, human papilloma virus E6, hTERT
*6 bmi, human papilloma virus E6, human papilloma virus E7, hTERT

TABLE 11

| Stem Cells | Sample Nos | Gene in LV | Value of Human - β-Actin | Relative index |
|---|---|---|---|---|
| Human Dental Pulp | Virus #1 | E7T*3 | 1.1715 | 1.00 |
| | Virus #2 | BT*4 | 0.2227 | 0.19 |
| | Virus #3 | BE6T*5 | 0.0960 | 0.08 |
| | Virus #4 | B6E7T*6 | 1.0422 | 0.89 |

(7) Results

Ct values calculated from the secondary differentiation curve of the real time PCR were plotted on X axis, and relative values of the total RNA were plotted on Y axis, respectively to prepare the calibration curved for each gene. From these calibration curves, the expression amount of each gene was calculated, and then variations among the samples were compensated by dividing the expression amount of each gene with that of β-actin, the internal standard gene, for each of them.

From the result of the real time PCR of the swine derived gene-introduced sample, the swine dental pulp stem cell with the transduced genes was introduced, showed the amplification of the transduced genes. In contrast, the cellos without them did not show such amplification. These mean that the genes introduced by using the lentivirus vector construct in Example 1 were expressed in the swine dental pulp stem cells to which those genes were transduced.

Figure 4:
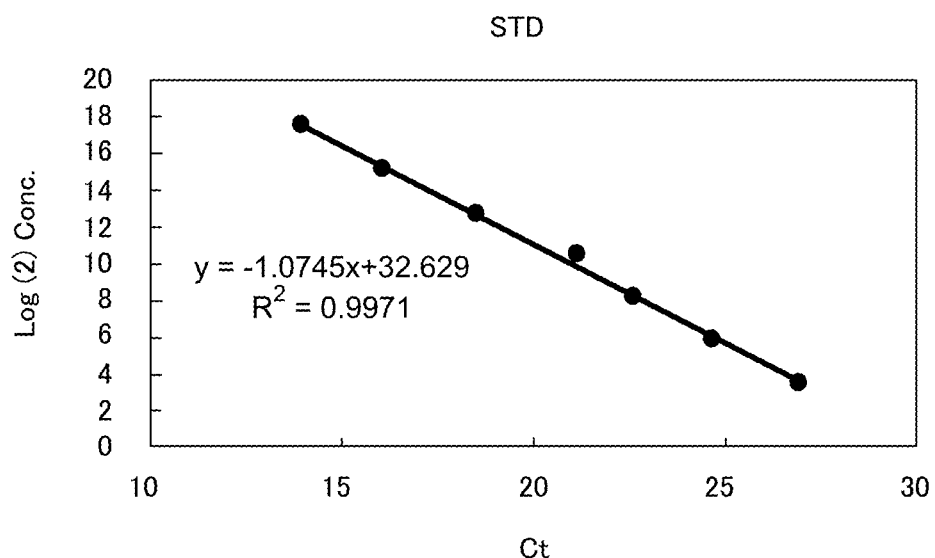
FIG. 4 is a calibration curve for obtaining an amplification amount of transfected genes after infection of the virus vector into a swine dental pulp stem cell or swine adipose stem cell.
Figure 5:
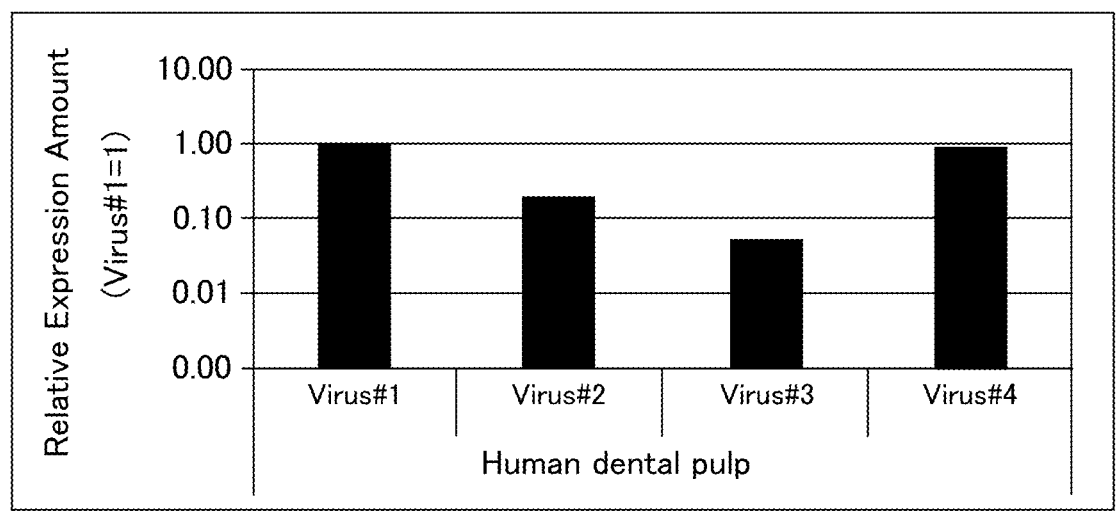
FIG. 5 is a graph showing relative index of the genes transfected after infection of the virus vector into a swine dental pulp stem cell or swine adipose stem cell.

Also, the results of the real time PCR of the swine derived gene-introduced sample showed that the internal standard genes were amplified. In FIGS. 4 and 5, the relative values of the respective transduced gene expression amount in the swine dental pulp stem cells or the swine adipose stem cells, when that of Virus #1 was 1. As far as the relative expression amount of the transduced genes, that of Virus #4 was closed to that of Virus #1. However, in other vectors, those were less than half of that of Virus #1. In the swine adipose stem cells, that of Virus #4 was almost 1 half of that of Virus #1; in Virus #2 or Virus #3, the expression amount was lower such as 1/3 to 1/5 of that of Virus #1.

Figure 6A:
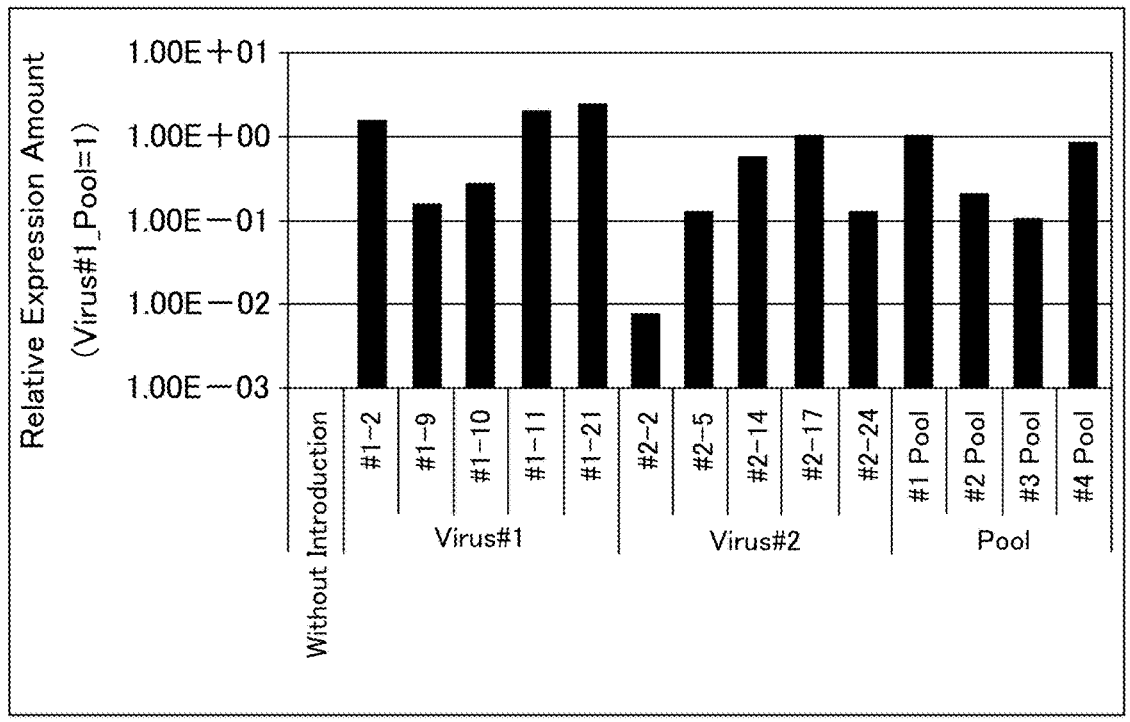
FIGS. 6A-6B show relative indexes of the gene expression amount in each cell populations (pool cell) or a cloned cell after gene introduction by using the virus vector.
Figure 6B:
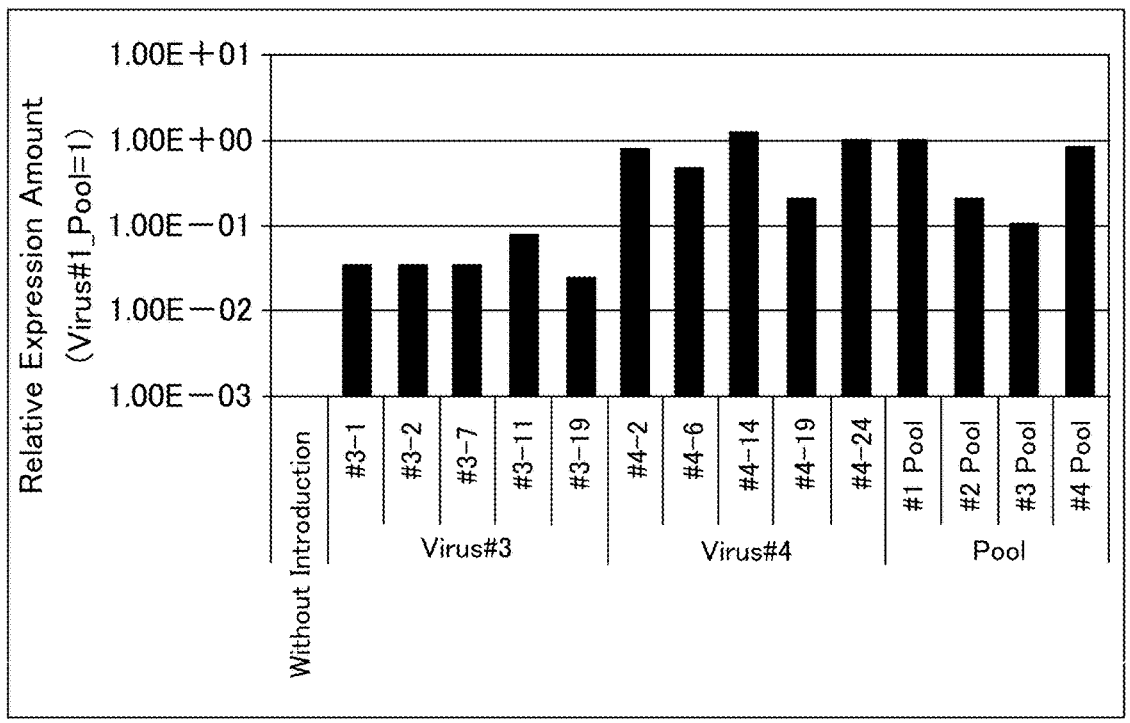

Table 10, FIG. 6 (A), and FIG. 6 (B) showed the expression statuses of genes in the human dental pulp stem cells. They showed that even in the human dental pulp stem cells, those of Virus #4 was more closed to those of Virus #1 similar to the cases of the stem cells from the swine. Also, it was shown that the expression ratios when other two vectors were used were lower such as less than 1/5 to 1/10, compared to the case of the swine stem cells.

As described above, it was confirmed that the expression efficiencies were different and have species difference, however, all of the transduced genes were expressed in the transduced cells.

(Example 6) Selection of the Gene Transduced Cell Line by Using the Drugs and Gene Expression Analysis (Preparation of the Pooled Cells)

(1) Preparation of the Retrovirus Vector Gene-Transduced Cells

The viable cells among the set up cells as described above were counted by using trypan blue staining and the hemocytometer. Then, they were plated in the dish having the diameter of 10 cm containing the culture medium at the concentration of $6 \times 10^6$ cells/10 mL, and then incubated at 37° C. in the $CO_2$ incubator for about 24 hours. When the cell density reached 70 to 90%, confluent, they were diluted to the concentration of $6 \times 10^4$ cells/mL for the passage. Mycoplasma infection was tested as described above, and all of the determination results were negative.

(2) Introduction of the Retrovirus Vector Genes and the Selection by Using the Drugs The retrovirus vectors constructed in Example 2 were infected to the stem cells obtained in Example 3 respectively, and they were cultured in the medium including GENETICIN for the selection of the stable expression cell lines of the target genes. Combinations of the genes in the retrovirus incorporating immortalization genes were as follows: in the cells A-1 and A-2, 3 genes (hTERT, HPV16_E6, and HPV16_E7); in the cell B-1 and B-2, 4 genes (hTERT, hBmi-1, HPV16_E6, and HPV16_E7). The retrovirus vector solution was prepared by diluting 4 timed for both of the cells A-1 and B-1; and prepared by diluting 10 times for both of A-2 and B-2.

Introduction of the retrovirus vector into each of the stem cells (the target cells), and the selection of the cells after the introduction of the vectors were conducted according to those in Example 5. The cell population after selected by using the drugs were collected as the drug resistant pooled cells and then cryopreserved. For the real time PCR analysis, the pellet including $5 \times 10^5$ cells were prepared and stored at −80° C.

(3) Preparation of Total RNA

The preparation of the total RNA was conducted by using NucleoSpin RNA II (the kit of MACHEREY-NAGEL) as the same as those in Example 5. Extraction results of the total RNA obtained from the pellets of respective cells are shown in the following Table 12.

TABLE 12

| Sample Nos. | Name of Cells | Conc. (µg/µL) | Absorbance A260 | Absorbance A280 | Relative Index 260/280 | Relative Index 260/230 | Yield (µg) |
|---|---|---|---|---|---|---|---|
| 1 | A-1 | 239.77 | 5.994 | 2.833 | 2.12 | 2.19 | 9.59 |
| 2 | A-2 | 277.83 | 6.946 | 3.275 | 2.12 | 2.19 | 11.11 |
| 3 | B-1 | 353.89 | 8.847 | 4.205 | 2.10 | 2.22 | 14.16 |
| 4 | B-2 | 219.66 | 5.492 | 2.587 | 2.12 | 2.19 | 8.79 |
| 5 | NT* | 332.44 | 8.311 | 3.867 | 2.15 | 2.31 | 13.30 |

*Target cell line without treatment (4) Reverse Transcription and the Real Time PCR (4-1) Reverse Transcription Reverse transcription was conducted by using the total RNA sample obtained as described above and the reverse transcription kit (PrimeScript RT reagent Kit (Perfect Real time, TaKaRa Bio)).

20 µL of the Premix (the reaction mixture) containing 4 µL of 5× PrimeScript buffer (final conc. was ×1), 1 µL of PrimeScript RT Enzyme Mix, 1 µL of Random 6 mer (100 µM, final conc. was 5 µM), 10 µL of the total RNA and 4 µL of the double distilled water (D2W). Next, the Premix was dispensed into the PCR tubes at 10 µL each, and 10 µL of the template RNA was added to them. Then they were subjected to the revers transcription under the conditions of at 37° C. for 15 minutes, at 85° C. for 5 seconds, and cooled to 4° C. The obtained products (the reverse transcription products) were subjected to the following real time PCR.

(4-2) The Real Time PCR by Using SYBR Premix Ex Taq

The Premix for real time PCR (25.0 µL) was prepared by mixing 12.5 µL of SYBR Premix Ex Taq II (×2, final conc. was ×1), 0.5 µL of PCR Primer mix (10 µM, final conc. was 0.2 µM of each), 2.0 µL of the reverse transcription solution, and 10.0 µL of the sterile distilled water. The primers were used at final concentration of 0.4 µM of each. As the reference gene, human β-action was used. The primers having the nucleotide sequences shown in Table 7 were used in PCR (Seq. Nos. 10 to 15 in the sequence listing); the reference samples were prepared as shown in Table 8.

The Premix was dispensed into the tubed for the real time PCR at 25 µL of each. Then, the real time PCR was conducted by using the real time PCR apparatus (Thermal Cycler Dice Real Time System: Takara Bio Inc.) under the conditions of at 95° C. for 30 seconds, and 40 cycles of (at 95° C. for 5 seconds, and then at 60° C. for 30 seconds). Subsequently, DNAs were denatured under the conditions of at 95° C. for 15 seconds, at 60° C. for 30 seconds, and 95° C. for 15 seconds to obtain the melting curve.

Figure 8:
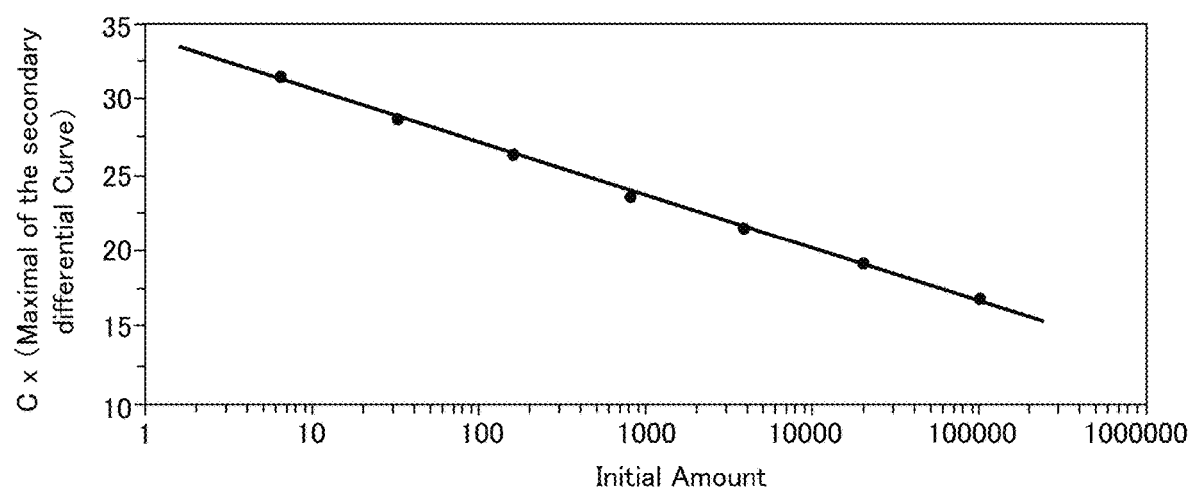
FIG. 8 is the calibration curve for obtaining the gene amplification amounts after the virus vector infection to the human dental pulp stem cells.

The melting curve is the graph composed of the temperature plotted on X axis and fluorescence intensity on Y axis, when the temperature is increased after PCR. Alternatively, the peak of the primary differentiation curve shows Tm value (melting temperature), which is the temperature that the double strand DNAs as the PCR amplification products are denatured into single strand DNAs, and it is an indicator that the amplified PCR products are not mixture. In the present example, human dental pulp stem cells were treated. Results were shown in the following Table 13, FIGS. 8 and 9 (n=2). The relative expression amount in Table 13 shows the relative expression amounts when that of the sample 1 was 1 after compensated with that of β-actin.

TABLE 13

| Sample | Total RNA Amount (pg) | RT | TERT Ct (SDM)*1 | TERT Calculate Value (pg) | Human β Actin Ct (SDM) | Human β Actin Calculate Value (pg) | TERT/β-Actin Normalization (Calculate Value) | TERT/β-Actin Relative expression value |
|---|---|---|---|---|---|---|---|---|
| STD 1 | 100,000 | + | 16.84 | 86010.0 | 12.54 | 86930.0 | 0.99 | |
| STD 2 | 20,000 | + | 19.13 | 19130.0 | 14.64 | 20830.0 | 0.92 | |
| STD 3 | 4,000 | + | 21.39 | 4344.0 | 16.94 | 4383.0 | 0.99 | |
| STD 4 | 800 | + | 23.70 | 953.9 | 19.36 | 856.0 | 1.11 | |
| STD 5 | 160 | + | 26.24 | 179.7 | 21.77 | 167.8 | 1.07 | |
| STD 6 | 32 | + | 28.77 | 34.3 | 24.30 | 30.2 | 1.14 | |
| STD 7 | 6.4 | + | 31.69 | 5.1 | 26.70 | 6.0 | 0.85 | |
| STD 8 | – | – | -- | -- | -- | -- | -- | -- |
| 1 | 20,000 | + | 18.80 | 23690.0 | 14.73 | 19620.0 | 1.21 | 1.00 |
| 2 | 20,000 | + | 18.96 | 21320.0 | 14.31 | 26040.0 | 0.82 | 0.68 |
| 3 | 20,000 | + | 19.14 | 18950.0 | 14.70 | 20000.0 | 0.95 | 0.78 |
| 4 | 20,000 | + | 19.63 | 13780.0 | 14.68 | 20270.0 | 0.68 | 0.56 |
| 5 | 20,000 | + | -- | -- | 15.23 | 13930.0 | -- | -- |

*1Secondary differentiation curve (the graph of fluorescence intensity of PCR products were twice differentiated)

(5) Results

Ct values calculated from the secondary differentiation curve of the real time PCR were plotted on X axis, and relative values of the total RNA were plotted on Y axis, respectively to prepare the calibration curved for each gene. From these calibration curves, the expression amount of each gene was calculated, and then variations among the samples were compensated by dividing the expression amount of each gene with that of β-actin, the internal standard gene, for each of them.

From the result of the real time PCR of the human derived gene-introduced sample, the human dental pulp stem cell with the transduced genes was introduced, showed the amplification of the transduced genes. In contrast, the cellos without them did not show such amplification. These mean that the genes introduced by using the lentivirus vector construct in Example 1 were expressed in the swine dental pulp stem cells to which those genes were transduced.

Figure 9:
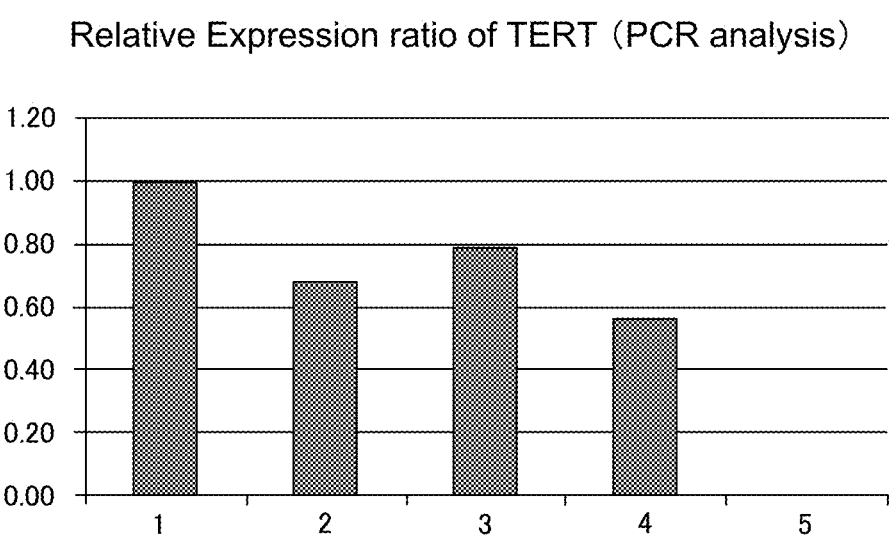
FIG. 9 is the graph for showing the relative index of the expression amounts of the gene (hTERT) after the retrovirus vector infection to the human dental pulp stem cells.
Figure 10C:
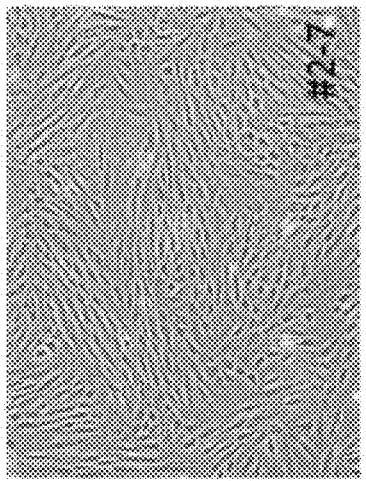
FIGS. 10A-10E microscope images after cultivation of the immortalized swine dental pulp stem cells or human dental pulp stem cells prepared by using the present method ((A) to (E)).
Figure 10B:
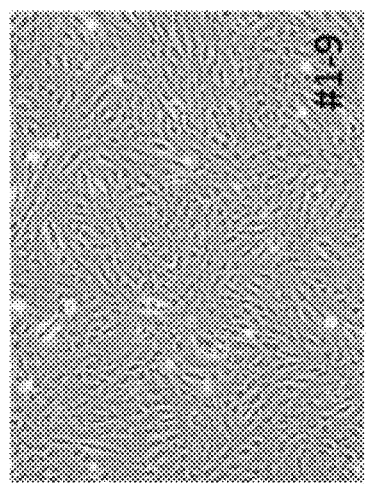
Figure 10E:
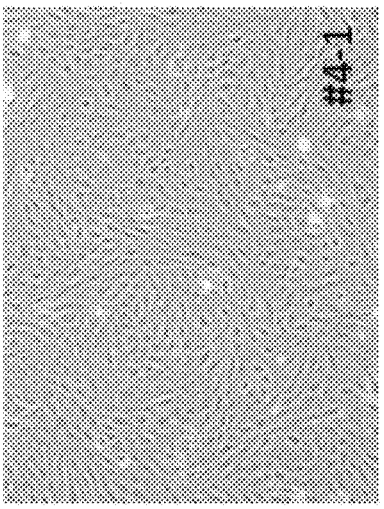
Figure 10A:
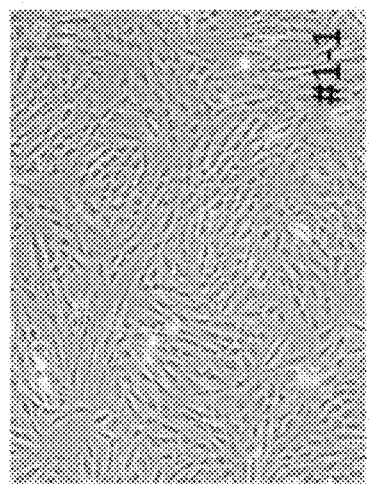
Figure 10D:
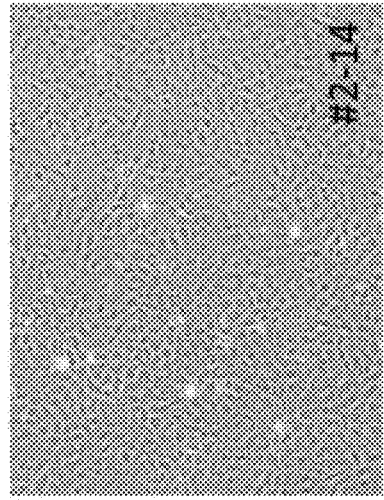

Also, the results of the real time PCR of the human derived gene-introduced sample showed that the internal standard genes. In FIG. 9, the relative value of the respective transduced gene expression amount in the human dental pulp stem cells, when that of the sample 1 was 1. As far as the relative expression amount of the transduced genes, that of the sample 3 was closed to that of the sample 1. However, in other two showed around 60%.

As shown in Table 13 and FIG. 9, it was confirmed that hTERT was expressed either case that 3 genes were introduced or 4 genes were introduced.

(Example 7) Single Cell Cloning and Gene Expression Analysis (1) Materials and Methods As the cells for the single cell cloning, the gene-transduced cells prepared in Example 5 were used. The culture medium, drugs for the selection, the kit or the reagent used for the real time PCR were the same as those used in Example 1 to Example 6. Culture method or other experimental procedures and other conditions were the same as those.

(2) Expansion Culture

The cell population stably expressing the introduced genes were plated into the dish having the diameter of 60 mm at the concentration of $1\times10^3$ cells/dish, and incubated in the $CO_2$ incubator at 37° C. for 24 hours. After that, the medium was exchanged to the growth medium (DMEM supplemented with 10% FBS) including the drug for the selection (G418) and cultured for forming colonies. As the same as those in Example 4 and Example 5, each of the colonies formed was released from the dish by using both of the cloning ring and the releasing agent, and then respectively inoculated in the 24-well plate. After growing them in the 24-well plate, they were plated into the dish having the diameter of 60 mm and then grown. Subsequently, they were plated in the dish having the diameter of 100 mm and then transferred to T-225 flask for expansion culture. The virus vectors used for the gene introduction were the same as described above.

(3) Results of the Single Cell Cloning

For the cell line derived from the swine adipose stem cells which stably express introduced genes, single cell cloning was conducted twice and 5 clones shown in the following Table 14 were obtained. For the cell line derived from the swine dens deciduous dental pulp stem cells which stably express introduced genes, the single cell cloning was conducted twice. However, all of the cells were died during the culture so that any clones were obtained.

On the other and, for the cell line derived from the human dens deciduous dental pulp stem cells, 5 clones shown in Table 14 were obtained by using one of Virus #1, Virus #3 or Virus #4, respectively. However, the cells infected by Virus #2 were enlarged and they were not grown until the necessary numbers during the expanding culture caused. Therefore, the procedures were stopped.

TABLE 14

| | Name of Clone | | | | |
|---|---|---|---|---|---|
| Derived from Swine Dental Pulp | Virus #1-1 | Virus #1-9 | Virus #2-7 | Virus #2-14 | Virus #4-1 |
| Derived from Human Dental Pulp | Virus #1-2 | Virus #1-9 | Virus #1-10 | Virus #1-11 | Virus #1-21 |
| | Virus #3-1 | Virus #3-2 | Virus #3-7 | Virus #3-11 | Virus #3-19 |
| | Virus #4-2 | Virus #4-6 | Virus #4-14 | Virus #4-19 | Virus #4-24 |

(4) Gene Expression Analysis

For the clone cell of these cell lines which stably express the gene obtained in above-mentioned (3), the expressions both of the introduced genes and implied standard genes were measured by using the real time PCR. As the same as Example 3, total RNA was prepared from about $5 \times 10^5$ cells of each clone shown in Table 14 by using NucleoSpin RNA. Obtained total RNA was used as the template, reverse transcription was conducted by using PrimeScript RT reagent Kit to obtain template cDNA.

After that, the real time PCR was conducted under the same conditions as those in Example 3 by using SYBR Premix Ex TaqII (Tli RNaseH Plus), specific primers against the introduced genes or the internal standard gene (Seq. Nos. 16 to 19 in the sequence listing), and the reverse transcription products as the template with the real time PCR apparatus (Thermal Cycler Dice Real Time System). Procedures were conducted according to the manual included in the kit.

(5) Results of the Introduced Gene Expressions

As the same as those in Example 5 Ct values calculated from the secondary differentiation curve of the real time PCR were plotted on X axis, and relative values of the total RNA were plotted on Y axis, respectively to prepare the calibration curved for each gene expression. Compensation for the validation among the samples was conducted as the same as those in Example 6(5).

The following Tables 15 to 17, and FIGS. 6 (A) and 6(B) show the relative values of the introduced gene expressions derived from the swine dental pulp stem cells, or the human dental pulp stem cells, when the expression amount of the genes in the pooled cells to be introduced the genes by using Virus #1 equals 1.

TABLE 15

|  | Titer | Relative Index of Total RNA (Log (2)) | Ct (STD) *1 |
|---|---|---|---|
| Calibration Curve | $1.00 \times 10^5$ | 16.6 | 16.68 |
|  | $2.00 \times 10^4$ | 14.3 | 18.95 |
|  | $4.00 \times 10^3$ | 12.0 | 21.25 |
|  | $8.00 \times 10^2$ | 9.6 | 23.71 |
|  | $1.60 \times 10^2$ | 7.3 | 25.99 |
|  | $3.20 \times 10^1$ | 5.0 | 28.21 |
|  | $6.40 \times 10^0$ | 2.7 | 30.87 |
|  | Slope |  | −1.074 |
|  | Segment |  | 32.629 |
|  | Amplification Efficiency |  | 0.997 |
|  | Relative index (R) |  | −1.000 |
|  | RSQ (Coefficient of Determination, $R^2$) |  | 1.000 |

*1: Obtained from an amplification curve (secondary differential curve) of the reference insert gene derived from swine.

TABLE 16

| Stem cells | Sample Nos. | Gene in LV | Average expression amount GOI/human β actin | Relative index |
|---|---|---|---|---|
| Swine dental pulp clone | Virus #1-1 | E7T*[3] | 1.22263 | 1.244 |
|  | Virus #1-9 | E7T*[3] | 1.22367 | 1.245 |
|  | Virus #2-7 | BT*[4] | 0.16424 | 0.167 |
|  | Virus #2-14 | BT*[4] | 0.24875 | 0.253 |
|  | Virus #4-1 | BE6T*[5] | 0.00126 | 0.001 |
| swine dental pulp pool | Virus #1 | E7T*[3] | 0.98276 | 1.000 |
|  | Virus #2 | BT*[4] | 0.36631 | 0.373 |
|  | Virus #3 | BE6T*[5] | 0.18431 | 0.188 |
|  | Virus #4 | B6E7T*[6] | 0.72732 | 0.740 |

TABLE 17

| Stem cells | Sample Nos. | Gene in LV | Average expression amount GOI/human β actin | Relative index |
|---|---|---|---|---|
| human dental pulp clone | Virus #1-2 | E7T*[3] | 1.8848 | 1.65 |
|  | Virus #1-9 | E7T*[3] | 0.1932 | 0.17 |
|  | Virus #1-10 | E7T*[3] | 0.3508 | 0.31 |
|  | Virus #1-11 | E7T*[3] | 2.6537 | 2.32 |
|  | Virus #1-22 | E7T*[3] | 3.0048 | 2.63 |
|  | Virus #2-2 | BT*[4] | 0.0094 | 0.01 |
|  | Virus #2-5 | BT*[4] | 0.1566 | 0.14 |
|  | Virus #2-14 | BT*[4] | 0.7429 | 0.65 |
|  | Virus #2-17 | BT*[4] | 0.8024 | 0.70 |
|  | Virus #2-24 | BT*[4] | 0.1639 | 0.14 |
|  | Virus #3-1 | BE6T*[5] | 0.0395 | 0.03 |
|  | Virus #3-2 | BE6T*[5] | 0.0437 | 0.04 |
|  | Virus #3-7 | BE6T*[5] | 0.0398 | 0.03 |
|  | Virus #3-11 | BE6T*[5] | 0.0857 | 0.07 |
|  | Virus #3-19 | BE6T*[5] | 0.0283 | 0.02 |
|  | Virus #4-2 | B6E7T*[6] | 0.8966 | 0.79 |
|  | Virus #4-6 | B6E7T*[6] | 0.5563 | 0.49 |
|  | Virus #4-14 | B6E7T*[6] | 1.4187 | 1.24 |
|  | Virus #4-19 | B6E7T*[6] | 0.2320 | 0.20 |
|  | Virus #4-24 | B6E7T*[6] | 1.2183 | 1.07 |
| human dental pulp pool | Virus #1 | E7T*[3] | 0.98276 | 1.00 |
|  | Virus #2 | BT*[4] | 0.36631 | 0.24 |
|  | Virus #3 | BE6T*[5] | 0.18431 | 0.12 |
|  | Virus #4 | B6E7T*[6] | 0.72732 | 0.84 |

From the above, it was shown that the introduced genes are expresses in all of the cell lines; the cell lines stably express the introduced genes derived from the human dens deciduous dental pulp stem cells. Alto the results showed that the expression amounts of the genes are very different depending on the genes introduced.

Also, FIGS. 10 (A) to (E) are the microscope images when the obtained clones were cultured. It was confirmed that all of the cell have almost equal sizes, and confluent without irregular sized cells, and they are normally grown.

INDUSTRIAL APPLICABILITY

The present invention is useful in the field of the pharmaceuticals and diagnostics.

SEQUENCE LISTING FREE TEXT

Seq. No. 1: Nucleotide sequence of the DNA fragment including genes to be inserted into the cells (1).
Seq. No. 2: Nucleotide sequence of the DNA fragment including genes to be inserted into the cells (2).
Seq. No. 3: Nucleotide sequence of the DNA fragment including genes to be inserted into the cells (3).
Seq. No. 4: Nucleotide sequence of the DNA fragment including genes to be inserted into the cells (4).
Seq. No. 5: Nucleotide sequence of the DNA fragment including genes to be inserted into the cells (5).
Seq. No. 6: Nucleotide sequence of the DNA fragment including genes to be inserted into the cells (1).
Seq. No. 7: Nucleotide sequence of the DNA fragment including genes to be inserted into the cells (7).
Seq. No. 8: Nucleotide sequence of the DNA fragment including genes to be inserted into the cells (8).
Seq. No. 9: Nucleotide sequence of the DNA fragment including genes to be inserted into the cells (9).
Seq. No. 10: Primer for PCR (1).
Seq. No. 11: Primer for PCR (2).
Seq. No. 12: Primer for PCR (3).
Seq. No. 13: Primer for PCR (4).

Seq. No. 14: Primer for PCR (5).
Seq. No. 15: Primer for PCR (6).
Seq. No. 16: Primer for PCR (7).
Seq. No. 17: Primer for PCR (8).
Seq. No. 18: Primer for PCR (9).
Seq. No. 19: Primer for PCR (10).

The invention claimed is:

1. A method for producing an immortalized stem cell comprising the steps of:
   producing DNA fragment comprising 3 genes selected from the group consisting of Bmi gene, human papilloma virus E6 gene and/or human papilloma virus E7 gene, and telomerase reverse transcriptase gene (TERT);
   constructing a virus vector into which said DNA fragment comprising said genes are inserted, wherein said genes comprise SEQ ID NO: 3 or SEQ ID NO: 4 when the virus vector is a lentivirus, selected from the group consisting of lentivirus plasmid vector pLVSIN-CMV Neo, Lenti Vector E7T, Lenti Vector BT, Lenti Vector BE6T, and Lenti Vector E6E7T, or said genes comprise 3 of SEQ ID NO: 5, 6, 7, 8, and 9 when the virus vector is a retrovirus, selected from the group consisting of pDON-5 Neo hTERT vector, pDON-5 Neo HPV16E6 vector, pDON-5 Neo HPV16E7 vector, pDON-5 Neo pHTERT vector, and pDON-5 Neo hBmil vector;
   introducing said genes into a mammal dental pulp stem cell by infecting said cell with a packaged virus vector produced from said virus vector DNA; and
   culturing said immortalized dental pulp stem cell to which said gene is introduced to select said immortalized stem cell by using a drug.

2. The method for producing an immortalized stem cell according to the claim 1, wherein said DNA fragment comprises any one of gene set selected from the group consisting of
   (a) bmi-1 gene, human papilloma virus E6 gene and TERT; and
   (b) human papilloma virus E6 gene, human papilloma virus E7 gene and TERT1.

3. The method for producing an immortalized stem cell according to claim 1, wherein said telomerase reverse transcriptase gene is derived from human or swine.

4. The method for producing an immortalized stem cell according to claim 1, wherein said mammal dental pulp stem cell is any one of the cells selected from the group consisting of a human dental pulp stem cell and a swine dental pulp stem cell.

5. The method for producing an immortalized stem cell according to claim 1, wherein said drug is GENETICIN.

6. The method for producing an immortalized stem cell according to the claim 1, further comprising the step of cloning said selected immortalized stem cell.

7. The immortalized stem cell expressing all of the genes introduced produced by any one of the methods for producing said immortalized stem cell claimed in claim 1.

8. The immortalized stem cell according to the claim 7, wherein said cell is capable of undergoing at least 200 PD.

9. The immortalized stem cell according to claim 7, wherein a STRO-1 expression amount thereof at 200 PD is almost equal to that of stem cell which is not immortalized.

10. The method for producing an immortalized stem cell according to claim 2, wherein said telomerase reverse transcriptase gene is derived from human or swine.

11. The method for producing an immortalized stem cell according to claim 2, wherein said drug is GENETICIN.

12. The method for producing an immortalized stem cell according to claim 3, wherein said drug is GENETICIN.

13. The method for producing an immortalized stem cell according to claim 1, wherein said drug is GENETICIN.

14. The immortalized stem cell expressing all of the genes introduced produced by any one of the method for producing said immortalized stem cell claimed in claim 2.

15. The immortalized stem cell expressing all of the genes introduced produced by any one of the method for producing said immortalized stem cell claimed in claim 3.

16. The immortalized stem cell expressing all of the genes introduced produced by any one of the method for producing said immortalized stem cell claimed in claim 1.

17. The immortalized stem cell according to the claim 8, wherein a STRO-1 expression amount thereof at 200 PD is almost equal to that of stem cell which is not immortalized.

* * * * *

```
                        SEQUENCE LISTING

<160> NUMBER OF SEQ ID NOS: 19

<210> SEQ ID NO 1
<211> LENGTH: 3928
<212> TYPE: DNA
<213> ORGANISM: Artifical Sequence
<220> FEATURE:
<223> OTHER INFORMATION: synthesized plasmid vector
<220> FEATURE:
<221> NAME/KEY: misc_feature
<222> LOCATION: (1)..(3928)
<223> OTHER INFORMATION: DNA fragment for gene transduction

<400> SEQUENCE: 1
acgctgtttt gacctccata gaagacaccg actctactag aggatctatt tccggtgaat      60
tcgccaccca tggagataca cctacattgc atgaatatat gttagatttg caaccagaga     120
caactgatct ctactgttat gagcaattaa atgacagctc agaggaggag gatgaaatag     180
atggtccagc tggacaagca gaaccggaca gagcccatta caatattgta acctttgtt     240 gcaagtgtga ctctacgctt cggttgtgcg tacaaagcac acacgtagac attcgtactt     300
tggaagacct gttaatgggc acactaggaa ttgtgtgccc catctgttct cagaaaccag     360
gatctgaagg tagggaagt ttgcttactt gcggtgacgt cgaagagaat ccaggaccag     420
atggccgcaa catgccgcgc gctccccgct gccgagccgt gcgctccctg ctgcgcagcc     480
actaccgcga ggtgctgccg ctggccacgt tcgtgcggcg cctggggccc cagggctggc     540
ggctggtgca gcgcggggac ccggcggctt tccgcgcgct ggtggcccag tgcctggtgt     600
gcgtgccctg ggacgcacgg ccgccccccg ccgccccctc cttccgccag gtgtcctgcc     660
tgaaggagct ggtggcccga gtgctgcaga ggctgtgcga gcgcgcgcg aagaacgtgc     720 tggccttcgg cttcgcgctg ctggacgggg cccgcggggg ccccccgag gccttcacca     780 ccagcgtgcg cagctacctg cccaacacgg tgaccgacgc actgcggggg agcggggcgt     840
gggggctgct gctgcgccgc gtgggcgacg acgtgctggt tcacctgctg gcacgctgcg     900
cgctctttgt gctggtggct cccagctgcg cctaccaggt gtgcgggccg ccgctgtacc     960
agctcggcgc tgccactcag gcccggcccc cgccacacgc tagtggaccc cgaaggcgtc    1020
tgggatgcga acgggcctgg aaccatagcg tcagggaggc cggggtcccc ctgggcctgc    1080 cagcccccggg tgcgaggagg cgcggggca gtgccagccg aagtctgccg ttgcccaaga    1140
ggcccaggcg tggcgctgcc cctgagccgg agcggacgcc cgttgggcag gggtcctggg    1200
cccacccggg caggacgcgt ggaccgagtg accgtggttt ctgtgtggtg tcacctgcca    1260
gacccgccga agaagccacc tctttggagg gtgcgctctc tggcacgcgc cactcccacc    1320
catccgtggg ccgccagcac cacgcgggcc cccatccac atcgcggcca ccacgtccct    1380
gggacacgcc ttgtcccccg gtgtacgccg agaccaagca cttcctctac tcctcaggcg    1440
acaaggagca gctgcggccc tccttcctac tcagctctct gaggcccagc ctgactggcg    1500
ctcggaggct cgtggagacc atctttctgg gttccaggcc ctgatgcca gggactcccc    1560 gcaggttgcc ccgcctgccc cagcgctact ggcaaatgcg ccctgtttt ctggagctgc    1620 ttgggaacca cgcgcagtgc ccctacgggg tgctcctcaa gacgcactgc ccgctgcgag    1680
ctgcggtcac cccagcagcc ggtgtctgtg cccgggagaa gccccagggc tctgtggcgg    1740
```

```
cccccgagga ggaggacaca gaccccccgtc gcctggtgca gctgctccgc cagcacagca    1800
gccccctggca ggtgtacggc ttcgtgcggg cctgcctgcg ccggctggtg cccccaggcc    1860
tctggggctc caggcacaac gaacgccgct tcctcaggaa caccaagaag ttcatctccc    1920
tggggaagca tgccaagctc tcgctgcagg agctgacgtg gaagatgagc gtgcgggact    1980
gcgcttggct gcgcaggagc ccaggggttg gctgtgttcc ggccgcagag caccgtctgc    2040
gtgaggagat cctggccaag ttcctgcact ggctgatgag tgtgtacgtc gtcgagctgc    2100
tcaggtctct cttttatgtc acggagacca cgtttcaaaa gaacaggctc ttttttctacc    2160
ggaagagtgt ctggagcaag ttgcaaagca ttggaatcag acagcacttg aagagggtgc    2220
agctgcggga gctgtcggaa gcagaggtca ggcagcatcg ggaagccagg cccgccctgc    2280
tgacgtccag actccgcttc atccccaagc ctgacgggct gcggccgatt gtgaacatgg    2340
actacgtcgt gggagccaga acgttccgca gagaaaagag ggccgagcgt ctcacctcga    2400
gggtgaaggc actgttcagc gtgctcaact acgagcgggc gcggcgcccc ggcctcctgg    2460
gcgcctctgt gctgggcctg gacgatatcc acagggcctg gcgcaccttc gtgctgcgtg    2520
tgcgggccca ggacccgccg cctgagctgt actttgtcaa ggtggatgtg acgggcgcgt    2580
acgacaccat ccccccaggac aggctcacgg aggtcatcgc cagcatcatc aaaccccaga    2640
acacgtactg cgtgcgtcgg tatgccgtgg tccagaaggc cgcccatggg cacgtccgca    2700
aggccttcaa gagccacgtc tctaccttga cagacctcca gccgtacatg cgacagttcg    2760
tggctcacct gcaggagacc agcccgctga gggatgccgt cgtcatcgag cagagctcct    2820
cccctgaatga ggccagcagt ggcctcttcg acgtcttcct acgcttcatg tgccaccacg    2880
ccgtgcgcat caggggcaag tcctacgtcc agtgccaggg gatcccgcag ggctccatcc    2940
tctccacgct gctctgcagc ctgtgctacg gcgacatgga gaacaagctg tttgcgggga    3000
ttcggcggga cgggctgctc ctgcgtttgg tggatgattt cttgttggtg acacctcacc    3060
tcacccacgc gaaaaccttc ctcaggaccc tggtccgagg tgtccctgag tatggctgcg    3120
tggtgaactt gcggaagaca gtggtgaact ccctgtagaa agacgaggcc ctgggtggca    3180
cggcttttgt tcagatgccg gcccacggcc tattccccctg gtgcggcctg ctgctggata    3240
cccggaccct ggaggtgcag agcgactact ccagctatgc ccggacctcc atcagagcca    3300
gtctcacctt caaccgcggc ttcaaggctg gaggaacat gcgtcgcaaa ctctttgggg    3360
tcttgcggct gaagtgtcac agcctgtttc tggatttgca ggtgaacagc ctccagacgg    3420
tgtgcaccaa catctacaag atcctcctgc tgcaggcgta caggtttcac gcatgtgtgc    3480
tgcagctccc atttcatcag caagtttgga agaacccccac attttttcctg cgcgtcatct    3540
ctgacacggc ctcctctgc tactccatcc tgaaagccaa gaacgcaggg atgtcgctgg    3600
gggccaaggg cgccgccggc cctctgccct ccgaggccgt gcagtggctg tgccaccaag    3660
cattcctgct caagctgact cgacaccgtg tcacctacgt gccactcctg ggtcactca    3720
ggacagccca gacgcagctg agtcggaagc tcccggggac gacgctgact gccctggagg    3780
ccgcagccaa cccggcactg ccctcagact tcaagaccat cctggactga ggatccaatt    3840
ctaccgggta ggggaggcgc ttttcccaag gcagtctgga gcatgcgctt tagcagcccc    3900
gctgggcact tggcgctaca caagtggc                                         3928
```

<210> SEQ ID NO 2
<211> LENGTH: 2556
<212> TYPE: DNA
<213> ORGANISM: Artificial Sequence
<220> FEATURE:
<223> OTHER INFORMATION: synthesized plasmid vectorr
<220> FEATURE:
<221> NAME/KEY: misc_feature
<222> LOCATION: (1)..(2556)

<400> SEQUENCE: 2

```
ccatccacgc tgttttgacc tccatagaag acaccgactc tactagagga tctatttccg      60
gtgaattcgc cacccatcga acaacgagaa tcaagatcac tgagctaaat ccccacctga     120
tgtgtgtgct ttgtggaggg tacttcattg atgccacaac cataatagaa tgtctacatt     180
ccttctgtaa aacgtgtatt gttcgttacc tggagaccag caagtattgt cctatttgtg     240
atgtccaagt tcacaagacc agaccactac tgaatataag gtcagataaa actctccaag     300
atattgtata caaattagtt ccagggcttt caaaaatga aatgaagaga agaagggatt      360
tttatgcagc tcatccttct gctgatgctg ccaatggctc taatgaagat agaggagagg     420
ttgcagatga agataagaga attataactg atgatgagat aataagctta tccattgaat     480
tctttgacca gaacagattg gatcggaaag taaacaaaga caaagagaaa tctaaggagg     540
aggtgaatga taaaagatac ttacgatgcc cagcagcaat gactgtgatg cacttaagaa     600
agtttctcag aagtaaaatg gacatacccta atactttcca gattgatgtc atgtatgagg     660
aggaaccttt aaaggattat tatacactaa tggatattgc ctacatttat acctggagaa     720
ggaatggtcc acttccattg aaatacagag ttcgacctac ttgtaaaaga atgaagatca     780
gtcaccagag agatggactg acaaatgctg gagaactgga aagtgactct gggagtgaca     840
aggccaacag cccagcagga ggtattccct ccacctcttc ttgtttgcct agccccagta     900
ctccagtgca gtctcctcat ccacagtttc ctcacatttc cagtactatg aatggaacca     960
gcaacagccc cagcggtaac caccaatctt cttttgccaa tagacctcga aaatcatcag    1020
taaatgggtc atcagcaact tcttctggtg gatctgaagg tagggggaagt ttgcttactt    1080
gcggtgacgt cgaagagaat ccaggaccag atggccgcaa catgccgcgc gctcccgct     1140
gccgagccgt gcgctccctg ctgcgcagcc actaccgcga ggtgctgccg ctggccacgt    1200
tcgtgcggcg cctggggccc cagggctggc ggctggtgca gcgcggggac ccggcggctt    1260
tccgcgcgct ggtggcccag tgcctggtgt gcgtgccctg ggacgcacgg ccgccccccg    1320
ccgcccctc cttccgccag gtgtcctgcc tgaaggagct ggtggcccga gtgctgcaga    1380
ggctgtgcga gcgcggcgcg aagaacgtgc tggccttcgg cttcgcgctg ctggacgggg    1440
cccgcggggg cccccccgag gccttcacca ccagcgtgcg cagctacctg cccaacacgg    1500
tgaccgacgc actgcggggg agcggggcgt ggggggctgct gctgcgccgc gtgggcgacg    1560
acgtgctggt tcacctgctg gcacgctgcg cgctctttgt gctggtggct cccagctgcg    1620
cctaccaggt gtgcgggccg ccgctgtacc agctcggcgc tgccactcag gcccggcccc    1680
cgccacacgc tagtggaccc cgaaggcgtc tgggatgcga acgggcctgg aaccatagcg    1740
tcagggaggc cggggtcccc ctgggcctgc cagccccggg tgcgaggagg cgcggggca     1800
gtgccagccg aagtctgccg ttcccaaga gggcccaggcg tggcgctgcc cctgagccgg    1860
agcggacgcc cgttgggcag gggtcctggg cccaccccggg caggacgcgt ggaccgagtg    1920
accgtggttt ctgtgtggtg tcacctgcca gacccgccga agaagccacc tctttggagg    1980
gtgcgctctc tggcacgcgc cactcccacc catccgtggg ccgccagcac cacgcgggcc    2040
ccccatccac atcgcggcca ccacgtccct gggacacgcg ttgtccccg gtgtacgccg     2100
agaccaagca cttcctctac tcctcaggcg acaaggagca gctgcggccc tccttcctac    2160
```

```
tcagctctct gaggcccagc ctgactggcg ctcggaggct cgtggagacc atctttctgg    2220
gttccaggcc ctggatgcca gggactcccc gcaggttgcc ccgcctgccc cagcgctact    2280
ggcaaatgcg gcccctgttt ctggagctgc ttgggaacca cgcgcagtgc ccctacgggg    2340
tgctcctcaa gacgcactgc ccgctgcgag ctgcggtcac cccagcagcc ggtgtctgtg    2400
cccgggagaa gccccagggc tctgtggcgg ccccgagga ggaggacaca gaccccgtc     2460 gcctggtgca gctgctccgc cagcacagca gcccctggca ggtgtacggc ttcgtgcggg    2520
cctgcctgcg ccggctggtg cccccaggcc tctggg                             2556

<210> SEQ ID NO 3
<211> LENGTH: 2983
<212> TYPE: DNA
<213> ORGANISM: Artificial Sequence
<220> FEATURE:
<223> OTHER INFORMATION: synthesized plasmid vector
<220> FEATURE:
<221> NAME/KEY: misc_feature
<222> LOCATION: (1)..(2983)

<400> SEQUENCE: 3
ccacgctgtt ttgacctcca tagaagacac cgactctact agaggatcta tttccggtga     60
attcgccacc catcgaacaa cgagaatcaa gatcactgag ctaaatcccc acctgatgtg    120
tgtgctttgt ggagggtact tcattgatgc cacaaccata atagaatgtc tacattcctt    180
ctgtaaaacg tgtattgttc gttacctgga gaccagcaag tattgtccta tttgtgatgt    240
ccaagttcac aagaccagac cactactgaa tataaggtca gataaaactc tccaagatat    300
tgtatacaaa ttagttccag ggcttttcaa aaatgaaatg aagagaagaa gggattttta    360
tgcagctcat ccttctgctg atgctgccaa tggctctaat gaagatagag gagaggttgc    420
agatgaagat aagagaatta taactgatga tgagataata agcttatcca ttgaattctt    480
tgaccagaac agattggatc ggaaagtaaa caaagacaaa gagaaatcta aggaggaggt    540
gaatgataaa agatacttac gatgcccagc agcaatgact gtgatgcact taagaaagtt    600
tctcagaagt aaaatggaca tacctaatac tttccagatt gatgtcatgt atgaggagga    660
acctttaaag gattattata cactaatgga tattgcctac atttatacct ggagaaggaa    720
tggtccactt ccattgaaat acagagttcg acctacttgt aaaagaatga agatcagtca    780
ccagagagat ggactgacaa atgctggaga actggaaagt gactctggga gtgacaaggc    840
caacagccca gcaggaggta ttccctccac ctcttcttgt ttgcctagcc ccagtactcc    900
agtgcagtct cctcatccac agtttcctca catttccagt actatgaatg gaaccagcaa    960
cagccccagc ggtaaccacc aatcttcttt tgccaataga cctcgaaaat catcagtaaa   1020
tgggtcatca gcaacttctt ctggtggatc tgaaggcaga ggctctctgc tgacatgtgg   1080
ggatgtggag gaaatcctg gccctacgcg tcaccaaaag agaactgcaa tgttccagga   1140
cccacaggag cgacccagaa agttaccaca gttatgcaca gagctgcaaa caactataca   1200
tgatataata ttagaatgtg tgtactgcaa gcaacagtta ctgcgacgtg aggtatatga   1260
ctttgctttt cgggatttat gcatagtata tagagatggg aatccatatg ctgtatgtga   1320
taaatgttta aagtttttatt ctaaaattag tgagtataga cattattgtt atagtttgta   1380
tggaacaaca ttagaacagc aatacaacaa accgttgtgt gatttgttaa ttaggtgtat   1440
taactgtcaa aagccactgt gtcctgaaga aaagcaaaga catctggaca aaaagcaaag   1500
attccataat ataaggggtc ggtggaccgg tcgatgtatg tcttgttgca gatcatcaag   1560
```

```
aacacgtaga gaaacccagc tgggatctga aggtagggga agtttgctta cttgcggtga    1620
cgtcgaagag aatccaggac cagatggccg caacatgccg cgcgctcccc gctgccgagc    1680
cgtgcgctcc ctgctgcgca gccactaccg cgaggtgctg ccgctggcca cgttcgtgcg    1740
gcgcctgggg ccccagggct ggcggctggt gcagcgcggg gacccggcgg ctttccgcgc    1800
gctggtggcc cagtgcctgg tgtgcgtgcc ctgggacgca cggccgcccc cgccgccccc    1860
ctccttccgc caggtgtcct gcctgaagga gctggtggcc cgagtgctgc agaggctgtg    1920
cgagcgcggc gcgaagaacg tgctggcctt cggcttcgcg ctgctggacg gggcccgcgg    1980 gggcccccc gaggccttca ccaccagcgt gcgcagctac ctgcccaaca cggtgaccga    2040
cgcactgcgg gggagcgggg cgtggggggct gctgctgcgc cgcgtgggcg acgacgtgct    2100
ggttcacctg ctggcacgct gcgcgctctt tgtgctggtg gctcccagct cgcctacca    2160 ggtgtgcggg ccgccgctgt accagctcgg cgctgccact caggcccggc ccccgccaca    2220
cgctagtgga ccccgaaggc gtctgggatg cgaacgggcc tggaaccata gcgtcaggga    2280
ggccggggtc ccctggggcc tgccagcccc gggtgcgagg aggcgcgggg gcagtgccag    2340
ccgaagtctg ccgttgccca agaggcccag gcgtggcgct gcccctgagc cggagcggac    2400
gcccgttggg caggggtcct gggcccaccc gggcaggacg cgtggaccga gtgaccgtgg    2460
tttctgtgtg gtgtcacctg ccagaccccgc cgaagaagcc acctctttgg agggtgcgct    2520
ctctggcacg cgccactccc acccatccgt gggccgccag caccacgcgg gccccccatc    2580
cacatcgcgg ccaccacgtc cctgggacac gccttgtccc ccggtgtacg ccagaccaa    2640 gcacttcctc tactcctcag gcgacaagga gcagctgcgg ccctccttcc tactcagctc    2700
tctgaggccc agcctgactg gcgctcggag gctcgtggag accatctttc tggggttccag    2760 gccctggatg ccagggactc cccgcaggtt gccccgcctg cccagcgct actggcaaat    2820 gcggccctg tttctggagc tgcttgggaa ccacgcgcag tgcccctacg gggtgctcct    2880
caagacgcac tgcccgctgc gagctgcggt caccccagca gccggtgtct gtgcccggga    2940
gaagccccag ggctctgtgg cggcccccga ggaggaggac aca                     2983
```

<210> SEQ ID NO 4
<211> LENGTH: 2223
<212> TYPE: DNA
<213> ORGANISM: Artificial Sequence
<220> FEATURE:
<223> OTHER INFORMATION: synthesized plasmid vector
<220> FEATURE:
<221> NAME/KEY: misc_feature
<222> LOCATION: (1)..(2223)

<400> SEQUENCE: 4

```
acgctgtttt gacctccata gaagacaccg actctactag aggatctatt tccggtgaat      60
tcgccaccca ccaaaagaga actgcaatgt tcaggaccc acaggagcga cccagaaagt     120
taccacagtt atgcacagag ctgcaaacaa ctatacatga tataatatta gaatgtgtgt     180
actgcaagca acagttactg cgacgtgagg tatatgactt tgcttttcgg gatttatgca     240
tagtatatag agatgggaat ccatatgctg tatgtgataa atgtttaaag ttttattcta     300
aaattagtga gtatagacat tattgttata gtttgtatgg aacaacatta gaacagcaat     360
acaacaaacc gttgtgtgat tgttaatta ggtgtattaa ctgtcaaaag ccactgtgtc     420
ctgaagaaaa gcaagacat ctggacaaaa agcaaagatt ccataatata aggggtcggt     480
ggaccggtcg atgtatgtct tgttgcagat catcaagaac acgtagagaa acccagctgg     540
```

```
gatctgaagg cagaggctct ctgctgacat gtggggatgt ggaggaaaat cctggcccta      600
cgcgtcatgg agatacacct acattgcatg aatatatgtt agatttgcaa ccagagacaa      660
ctgatctcta ctgttatgag caattaaatg acagctcaga ggaggaggat gaaatagatg      720
gtccagctgg acaagcagaa ccggacagag cccattacaa tattgtaacc ttttgttgca      780
agtgtgactc tacgcttcgg ttgtgcgtac aaagcacaca cgtagacatt cgtactttgg      840
aagacctgtt aatgggcaca ctaggaattg tgtgccccat ctgttctcag aaaccaggat      900
ctgaaggtag gggaagtttg cttacttgcg gtgacgtcga agagaatcca ggaccagatg      960
gccgcaacat gccgcgcgct ccccgctgcc gagccgtgcg ctccctgctg cgcagccact     1020
accgcgaggt gctgccgctg ccacgttcg tgcggcgcct ggggccccag gctggcggc      1080 tggtgcagcg cggggacccg gcggctttcc gcgcgctggt ggcccagtgc ctggtgtgcg     1140
tgccctggga cgcacggccg ccccccgccg cccctcctt ccgccaggtg tcctgcctga      1200
aggagctggt ggcccgagtg ctgcagaggc tgtgcgagcg cggcgcgaag aacgtgctgg     1260
ccttcggctt cgcgctgctg gacggggccc gcggggcccc cccgaggcc ttcaccacca      1320 gcgtgcgcag ctacctgccc aacacggtga ccgacgcact gcgggggagc ggggcgtggg     1380
ggctgctgct gcgccgcgtg ggcgacgacg tgctggttca cctgctggca cgctgcgcgc     1440
tctttgtgct ggtggctccc agctgcgcct accaggtgtg cgggccgccg ctgtaccagc     1500
tcggcgctgc cactcaggcc cggccccgc cacacgctag tggaccccga aggcgtctgg     1560
gatgcgaacg ggcctggaac catagcgtca gggaggccgg ggtcccctg gcctgccag      1620 ccccgggtgc gaggaggcgc ggggcagtg ccagccgaag tctgccgttg cccaagaggc     1680
ccaggcgtgg cgctgcccct gagccggagc ggacgcccgt tgggcagggg tcctgggccc     1740
acccgggcag gacgcgtgga ccgagtgacc gtggtttctg tgtggtgtca cctgccagac     1800
ccgccgaaga agcccctct ttggagggtg cgctctctgg cacgcgccac tcccaccat      1860 ccgtgggccg ccagcaccac gcgggccccc catccacatc gcggccacca cgtccctggg     1920
acacgccttg tccccggtg tacgccgaga ccaagcactt cctctactcc tcaggcgaca     1980
aggagcagct gcgcgccctcc ttcctactca gctctctgag gccagcctg actggcgctc     2040 ggaggctcgt ggagaccatc tttctggggtt ccaggccctg gatgccaggg actccccgca     2100
ggttgccccg cctgccccag cgctactggc aaatgcggcc cctgtttctg gagctgcttg     2160
ggaaccacgc gcagtgcccc tacgggggtgc tcctcaagac gcactgcccg ctgcgagctg     2220
cgg                                                                  2223

<210> SEQ ID NO 5
<211> LENGTH: 3399
<212> TYPE: DNA
<213> ORGANISM: Homo sapiens
<220> FEATURE:
<221> NAME/KEY: gene
<222> LOCATION: (1)..(3399)
<223> OTHER INFORMATION: hTERT, DNA fragment for gene transduction

<400> SEQUENCE: 5
atgccgcgcg ctccccgctg ccgagccgtg cgctccctgc tgcgcagcca ctaccgcgag       60
gtgctgccgc tggccacgtt cgtgcgcgcg ctggggcccc agggctggcg gctggtgcag      120
cgcggggacc cggcggcttt ccgcgcgctg gtggcccagt gcctggtgtg cgtgccctgg      180
gacgcacggc cgcccccgc cgcccctcc ttccgccagg tgtcctgcct gaaggagctg       240
```

-continued

```
gtggcccgag tgctgcagag gctgtgcgag cgcggcgcga agaacgtgct ggccttcggc    300
ttcgcgctgc tggacggggc ccgcgggggc ccccccgagg ccttcaccac cagcgtgcgc    360
agctacctgc ccaacacggt gaccgacgca ctgcggggga gcggggcgtg ggggctgctg    420
ctgcgccgcg tggcgacga cgtgctggtt cacctgctgg cacgctgcgc gctcttgtg     480 ctggtggctc ccagctgcgc ctaccaggtg tgcgggccgc cgctgtacca gctcggcgct    540
gccactcagg cccggccccc gccacacgct agtggacccc gaaggcgtct gggatgcgaa    600
cgggcctgga accatagcgt cagggaggcc ggggtccccc tgggcctgcc agccccgggt    660
gcgaggaggc gcggggggcag tgccagccga agtctgccgt tgcccaagag gcccaggcgt    720
ggcgctgccc ctgagccgga gcggacgccc gttgggcagg ggtcctgggc ccacccgggc    780
aggacgcgtg gaccgagtga ccgtggtttc tgtgtggtgt cacctgccag acccgccgaa    840
gaagccacct ctttggaggg tgcgctctct ggcacgcgcc actcccaccc atccgtgggc    900
cgccagcacc acgcgggccc cccatccaca tcgcggccac cacgtccctg ggacacgcct    960
tgtcccccgg tgtacgccga gaccaagcac ttcctctact cctcaggcga caaggagcag    1020
ctgcggccct ccttcctact cagctctctg aggcccagcc tgactggcgc tcggaggctc    1080
gtggagacca tctttctggg ttccaggccc tggatgccag ggactccccg caggttgccc    1140
cgcctgcccc agcgctactg gcaaatgcgg cccctgtttc tggagctgct tgggaaccac    1200
gcgcagtgcc cctacggggt gctcctcaag acgcactgcc cgctgcgagc tgcggtcacc    1260
ccagcagccg gtgtctgtgc ccgggagaag ccccagggct ctgtggcggc ccccgaggag    1320
gaggacacag acccccgtcg cctggtgcag ctgctccgcc agcacagcag ccctggcag    1380 gtgtacggct tcgtgcgggc ctgcctgcgc cggctggtgc ccccaggcct ctggggctcc    1440
aggcacaacg aacgccgctt cctcaggaac accaagaagt tcatctccct ggggaagcat    1500
gccaagctct cgctgcagga gctgacgtgg aagatgagcg tgcgggactg cgcttggctg    1560
cgcaggagcc caggggttgg ctgtgttccg gccgcagagc accgtctgcg tgaggagatc    1620
ctggccaagt tcctgcactg gctgatgagt gtgtacgtcg tcgagctgct caggtctttc    1680
ttttatgtca cggagaccac gtttcaaaag aacaggctct ttttctaccg gaagagtgtc    1740
tggagcaagt tgcaaagcat tggaatcaga cagcacttga agagggtgca gctgcgggag    1800
ctgtcggaag cagaggtcag gcagcatcgg gaagccaggc ccgccctgct gacgtccaga    1860
ctccgcttca tccccaagcc tgacgggctg cggccgattg tgaacatgga ctacgtcgtg    1920
ggagccagaa cgttccgcag agaaaagagg gccgagcgtc tcacctcgag ggtgaaggca    1980
ctgttcagcg tgctcaacta cgagcgggcg cggcgccccg gcctcctggg cgcctctgtg    2040
ctgggcctgg acgatatcca cagggcctgg cgcaccttcg tgctgcgtgt gcgggcccag    2100
gacccgccgc ctgagctgta ctttgtcaag gtggatgtga cgggcgcgta cgacaccatc    2160
ccccaggaca ggctcacgga ggtcatcgcc agcatcatca accccagaa cacgtactgc    2220 gtgcgtcggt atgccgtggt ccagaaggcc gcccatgggc acgtccgcaa ggccttcaag    2280
agccacgtct ctaccttgac agacctccag ccgtacatgc gacagttcgt ggctcacctg    2340
caggagacca gcccgctgag ggatgccgtc gtcatcgagc agagctcctc cctgaatgag    2400
gccagcagtg gcctcttcga cgtcttccta cgcttcatgt gccaccacgc cgtgcgcatc    2460
aggggcaagt cctacgtcca gtgccagggg atcccgcagg gctccatcct ctccacgctg    2520
ctctgcagcc tgtgctacgg cgacatggag aacaagctgt ttgcggggat cggcggac    2580 gggctgctcc tgcgtttggt ggatgatttc ttgttggtga cacctcacct cacccacgcg    2640
```

```
aaaaccttcc tcaggaccct ggtccgaggt gtccctgagt atggctgcgt ggtgaacttg    2700
cggaagacag tggtgaactt ccctgtagaa gacgaggccc tgggtggcac ggcttttgtt    2760
cagatgccgg cccacggcct attccctgg tgcggcctgc tgctggatac ccggaccctg    2820
gaggtgcaga gcgactactc cagctatgcc cggacctcca tcagagccag tctcaccttc    2880
aaccgcggct tcaaggctgg gaggaacatg cgtcgcaaac tctttggggt cttgcggctg    2940
aagtgtcaca gcctgtttct ggatttgcag gtgaacagcc tccagacggt gtgcaccaac    3000
atctacaaga tcctcctgct gcaggcgtac aggtttcacg catgtgtgct gcagctccca    3060
tttcatcagc aagtttggaa gaaccccaca tttttcctgc gcgtcatctc tgacacggcc    3120
tccctctgct actccatcct gaaagccaag aacgcaggga tgtcgctggg ggccaagggc    3180
gccgccggcc ctctgccctc cgaggccgtg cagtggctgt gccaccaagc attcctgctc    3240
aagctgactc gacaccgtgt cacctacgtg ccactcctgg ggtcactcag gacagcccag    3300
acgcagctga gtcggaagct cccggggacg acgctgactg ccctggaggc cgcagccaac    3360
ccggcactgc cctcagactt caagaccatc ctggactga                          3399

<210> SEQ ID NO 6
<211> LENGTH: 477
<212> TYPE: DNA
<213> ORGANISM: Human papillomavirus type 16
<220> FEATURE:
<221> NAME/KEY: gene
<222> LOCATION: (1)..(477)
<223> OTHER INFORMATION: HPV16 E6

<400> SEQUENCE: 6
atgcaccaaa agagaactgc aatgtttcag gacccacagg agcgacccag aaagttacca     60
cagttatgca cagagctgca acaactata catgatataa tattagaatg tgtgtactgc    120
aagcaacagt tactgcgacg tgaggtatat gactttgctt ttcgggattt atgcatagta    180
tatagagatg gaatccata tgctgtatgt gataaatgtt taaagtttta ttctaaaatt    240
agtgagtata gacattattg ttatagtttg tatggaacaa cattagaaca gcaatacaac    300
aaaccgttgt gtgatttgtt aattaggtgt attaactgtc aaaagccact gtgtcctgaa    360
gaaaagcaaa gacatctgga caaaaagcaa agattccata atataagggg tcggtggacc    420
ggtcgatgta tgtcttgttg cagatcatca agaacacgta gagaacccca gctgtaa     477

<210> SEQ ID NO 7
<211> LENGTH: 297
<212> TYPE: DNA
<213> ORGANISM: Human papillomavirus type 16
<220> FEATURE:
<221> NAME/KEY: gene
<222> LOCATION: (1)..(297)
<223> OTHER INFORMATION: HPV 16 E7, gene for transduction

<400> SEQUENCE: 7
atgcatggag atacacctac attgcatgaa tatatgttag atttgcaacc agagacaact     60
gatctctact gttatgagca attaaatgac agctcagagg aggaggatga aatagatggt    120
ccagctggac aagcagaacc ggacagagcc cattacaata ttgtaacctt ttgttgcaag    180
tgtgactcta cgcttcggtt gtgcgtacaa agcacacacg tagacattcg tactttggaa    240
gacctgttaa tgggcacact aggaattgtg tgccccatct gttctcagaa accataa      297

<210> SEQ ID NO 8
```

```
<211> LENGTH: 3396
<212> TYPE: DNA
<213> ORGANISM: Artificial Sequence
<220> FEATURE:
<221> NAME/KEY: pigTERT gene
<222> LOCATION: (1)..(3396)
<223> OTHER INFORMATION: pigTERT, DNA fragment for gene transduction

<400> SEQUENCE: 8
atgccgcgcg cgccccggtg ccgggccgtg cgctccctgc tccgggaccg ctacaggcag        60
gtgctgccgc tggccacctt cgtgcggcgc ctgggccctg agggccggcg gcttgttcgg       120
cgcggggacc cggcggccta ccgcgcgctg gtggcgcagt gcctggtgtg cgtgccctgg       180
gacgcgcagc cgcctcctgc ctccccgtcc ttccgccagg tgtcctgcct gaaggagctg       240
gtggccaggg tcgtgcagag gctctgcgag cgcggcgcga ggaacgtgct ggcctttggc       300
ttcgcgctgc tggacggggc tcgcggcggg ccgcccgtgg ccttcacgac cagcgtgcgc       360
agctacctgc ccaacaccgt gaccgacaca ctgcgcggga cggcgcgtg ggggctgctg        420 ctgcgccgcg tgggcgacga cgtgctcacc cacctgttgg cgcgctgcgc gctgtacctg       480
ctggtgcccc cgagttgcgc ctaccaggtg tgcgggccgc cactctatga cctctacacc       540
gcagcggagg ctcggcccat gcgacacaag ggccagaccc cgactggcct cggactcacg       600
cgccccgttt gcaatgggga agccgggcga ccccaggagc agagggcgca aggtgtgagg       660
cgacgtcggg gcagagcggg gggacatcca cttccagcca agaggccag gcacgtcccg        720 gagcctgaac agggtcccga agggcaggcg tcccgggccc accagggcag ggcgcctggg       780
ccgagcgaca gcgaccccc cgtgatgaca cctaccagag ccgctgcgaa agccaagtct        840
cgggagggtg aggcgcccgg aacccggcac cttttcccctc aagcaggcgg tgcgcggggt      900
acctgccccc catcctggtg gcagccacac ctccagggca agcccagtcc tcatgtgtgc       960
gctgccgaga ccaagcgctt cctctactgc tcggggagca aggaagggct gcgccgctcg      1020
ttcctgctct gctcccctgcc gcccagcctg gcggggccg gaggctcgt ggaggtcatc       1080 tttctggcct caaagcccgg gcagccaggg gcgcgccgcg tgcccgcacg ctactggcgg      1140
atgaggcccc tgttccggga gctgcttaag aaccacgcgc ggtgccccta caaggcgctt      1200
ctcagggcgc actgcccgtt gcgggctgcg gcgaccctct cggggtccgg cggtcaggtg      1260
tgcgaccaca aagtgggccc cctcgctcca gagcggctgg cagcgccgc cgaggggac       1320 tcggcctcga ggcgcctagt ccagctgctc cgccagcaca gcagccctg gcaggtgtac      1380 cgcctcctgc gggcctgtct tcaccggctg gtgcccccgg gcctctgggg ctccccgcac      1440
aacaagcggc gctttctgaa gaatgtgaag aagctcgtct ccctggggaa gcacgccagg      1500
ctctcgctgc aggagctgat gtggaagatg aaagtgcaag actgcatctg gctgcgccgg      1560
agcccggacg ctcgccatgt ccaggccgcc gagcaccgtc tgagagaggc cattctggcc      1620
aagttcctgc gctggttgat gggcacgtac gtggtcgagc tgctcaggtc gttttttttat     1680 gtcacggaga ccacgtttca gaagaaccgg ctcttcttct ccggaagcg catctggagc      1740 cggctgcaga gcgcaggcat caggcaacac ttagatcgtg tgcggcttcg agaactgtcg     1800
gaagcagaga tcaggcgacg ccgggaggcc aggcccgctg tactgacctc caagctccgc      1860
ttcgtcccca aacccgacgg gctgcggccc atcgtgaaca tggcgaacgt cgtgcgagcc      1920
aggacaggcc ccggagacaa gaaggtccgg cgtctcacgg ggcaggtcaa gacgctgttt      1980
gctgtgctga actacgagcg ggcgcggcgc ccgcgcctcc tggggcctc cgtgctggc       2040 gtgggtgaca tccacagggc gtggcgggcc tttgtgctgc ccctgcgggc ccaggacccg     2100
```

```
gccccccgc tgtactttgt caaggtggac gtgacggggg cctacgacgc cctccctcag    2160
gacaggcttg ctgaggtggt cgccaacgtg atccggccct acgagagcac gtactgcgtg    2220
cgccagtgcg ccgtgctccg gaggaccgcc cgcgggcacg tgcgcaagtc cttccaaacc    2280
cacgtgtcca ccttcgcaga cctccagcct tacatgagac agtttgtggc acacctgcag    2340
gcaaccggcc cgctgaggga cgccgtggtc atcgagcaga gctgctctct gaacgaggcc    2400
ggcagccgtc cctggagct tttcctgagc ctgctgcgaa accacgtcat ccggatcggg    2460
ggcaggtcct acgtccagtg tcaggggatc ccacagggct ccattctgtc cacgctgctc    2520
tgcagcctgt gctacgggga catggaaaac agactgtccc cggggatcca gcgtgacggg    2580
gtgctcctgc gcttggtgga cgacttcctg ctggtgaccc ctcacctgac acgagccaaa    2640
gcctttctca ggaccctggt ccgcggcgtg cccgagtacg gctgcctggc caacttgcgg    2700
aagacggccg tgaacttccc tgtggaggac ggcgcccggg gcggcccggc cccactgcag    2760
ctgccggcac actgcctgtt ccctggtgc gggctgctgc tggacacccg cacgctggag    2820
gtgcactgcg actatgccag ttacgcccgg acctcgatca gagcgagtct caccttcaac    2880
cagggcttca gcccgggag gaacatgcgc cgcaagctct tggcggtctt gcggctaaag    2940
tgccacggga tccttctgga cctgcaggtg aacagtcttc gacggtgct cgccaacgtt    3000 tacaagatct tcctgctgca ggcctacagg ttccacgcgt gtgtgctgca gctgcccttc    3060
cgtcagccgc ttgcgaggaa ccctcattt ttcctccggc ttgtctccga caccgcgtcc    3120
tgctgctact cgctcctgaa agccagaaac gcagggatgt ccctgggagc caggggcgcc    3180
tccggcccgt ttccctctga agccgcagag tggctctgcc tccacgcctt cctgctcaag    3240
ctggttcgtc accgcgttac ctacagctgt cttctggggc cgctccgggc agccagagag    3300
cgattgtgcc agcggctccc tggggccaca ctggccgccc tcgaggccgc cgccgaccca    3360
gccctgacta cagacttccg gaccatcctg gactga                              3396
```

<210> SEQ ID NO 9
<211> LENGTH: 981
<212> TYPE: DNA
<213> ORGANISM: Homo sapiens
<220> FEATURE:
<221> NAME/KEY: gene
<222> LOCATION: (1)..(981)
<223> OTHER INFORMATION: hbmi1, DNA fragment for gene transduction

<400> SEQUENCE: 9

```
atgcatcgaa caacgagaat caagatcact gagctaaatc cccacctgat gtgtgtgctt      60
tgtggagggt acttcattga tgccacaacc ataatagaat gtctacattc cttctgtaaa     120
acgtgtattg ttcgttacct ggagaccagc aagtattgtc ctatttgtga tgtccaagtt     180
cacaagacca gaccactact gaatataagg tcagataaaa ctctccaaga tattgtatac     240
aaattagttc cagggctttt caaaaatgaa atgaagagaa gagggatttt ttatgcagct     300 catcccttctg ctgatgctgc caatggctct aatgaagata gaggagaggt tgcagatgaa     360
gataagagaa ttataactga tgatgagata taagcttat ccattgaatt ctttgaccag     420
aacagattgg atcggaaagt aaacaaagac aagagagaat ctaaggagga ggtgaatgat     480
aaaagatact tacgatgccc agcagcaatg actgtgatgc acttaagaaa gtttctcaga     540
agtaaaatgg acatacctaa tactttccag attgatgtca tgtatgagga ggaaccttta     600
aaggattatt atacactaat ggatattgcc tacatttata cctggagaag gaatggtcca     660
```

-continued

```
cttccattga aatacagagt tcgacctact tgtaaaagaa tgaagatcag tcaccagaga    720
gatggactga caaatgctgg agaactggaa agtgactctg ggagtgacaa ggccaacagc    780
ccagcaggag gtattccctc cacctcttct tgtttgccta gccccagtac tccagtgcag    840
tctcctcatc cacagtttcc tcacatttcc agtactatga atggaaccag caacagcccc    900
agcggtaacc accaatcttc ttttgccaat agacctcgaa aatcatcagt aaatgggtca    960
tcagcaactt cttctggttg a                                              981
```

```
<210> SEQ ID NO 10
<211> LENGTH: 20
<212> TYPE: DNA
<213> ORGANISM: Artificial Sequence
<220> FEATURE:
<223> OTHER INFORMATION: one of primers in SYBR Premix Ex TaqII
<220> FEATURE:
<221> NAME/KEY: primer_bind
<222> LOCATION: (1)..(20)

<400> SEQUENCE: 10
ggcactgccc tcagacttca                                                 20

<210> SEQ ID NO 11
<211> LENGTH: 20
<212> TYPE: DNA
<213> ORGANISM: Artificial Sequence
<220> FEATURE:
<223> OTHER INFORMATION: one of primers in SYBR Premix Ex TaqII
<220> FEATURE:
<221> NAME/KEY: primer_bind
<222> LOCATION: (1)..(20)

<400> SEQUENCE: 11
ctgctaaagc gcatgctcca                                                 20

<210> SEQ ID NO 12
<211> LENGTH: 19
<212> TYPE: DNA
<213> ORGANISM: Artificial Sequence
<220> FEATURE:
<223> OTHER INFORMATION: one of primers in SYBR Premix Ex TaqII
<220> FEATURE:
<221> NAME/KEY: primer_bind
<222> LOCATION: (1)..(19)

<400> SEQUENCE: 12
ctgcggcatc cacgaacta                                                  19

<210> SEQ ID NO 13
<211> LENGTH: 19
<212> TYPE: DNA
<213> ORGANISM: Artificial Sequence
<220> FEATURE:
<223> OTHER INFORMATION: one of primers in SYBR Premix Ex TaqII
<220> FEATURE:
<221> NAME/KEY: primer_bind
<222> LOCATION: (1)..(19)

<400> SEQUENCE: 13
acagcaccgt gttggcgta                                                  19

<210> SEQ ID NO 14
<211> LENGTH: 24
<212> TYPE: DNA
<213> ORGANISM: Artificial Sequence
<220> FEATURE:
<223> OTHER INFORMATION: one of primers in SYBR Premix Ex TaqII
```

```
<220> FEATURE:
<221> NAME/KEY: primer_bind
<222> LOCATION: (1)..(24)

<400> SEQUENCE: 14
ttggtcaagc agcataatcc aaag                                              24

<210> SEQ ID NO 15
<211> LENGTH: 23
<212> TYPE: DNA
<213> ORGANISM: Artificial Sequence
<220> FEATURE:
<223> OTHER INFORMATION: one of primers in SYBR Premix Ex TaqII
<220> FEATURE:
<221> NAME/KEY: primer_bind
<222> LOCATION: (1)..(23)

<400> SEQUENCE: 15
gtcaagggca tagcctacca caa                                               23

<210> SEQ ID NO 16
<211> LENGTH: 22
<212> TYPE: DNA
<213> ORGANISM: Artificial Sequence
<220> FEATURE:
<223> OTHER INFORMATION: specific primer for real time PCR
<220> FEATURE:
<221> NAME/KEY: primer_bind
<222> LOCATION: (1)..(22)

<400> SEQUENCE: 16
gcactgccct cagacttcaa ga                                                22

<210> SEQ ID NO 17
<211> LENGTH: 20
<212> TYPE: DNA
<213> ORGANISM: Artificial Sequence
<220> FEATURE:
<223> OTHER INFORMATION: specific primer for real time PCR
<220> FEATURE:
<221> NAME/KEY: primer_bind
<222> LOCATION: (1)..(20)

<400> SEQUENCE: 17
gcgggactat ggttgctgac                                                   20

<210> SEQ ID NO 18
<211> LENGTH: 19
<212> TYPE: DNA
<213> ORGANISM: Artificial Sequence
<220> FEATURE:
<223> OTHER INFORMATION: specific primer for real time PCR
<220> FEATURE:
<221> NAME/KEY: primer_bind
<222> LOCATION: (1)..(19)

<400> SEQUENCE: 18
tggcacccag cacaatgaa                                                    19
```

```
<210> SEQ ID NO 19
<211> LENGTH: 25
<212> TYPE: DNA
<213> ORGANISM: Artificial Sequence
<220> FEATURE:
<223> OTHER INFORMATION: specific primer for real time PCR
<220> FEATURE:
<221> NAME/KEY: primer_bind
<222> LOCATION: (1)..(25)

<400> SEQUENCE: 19
ctaagtcata gtccgcctag aagca                                              25
```